(12) United States Patent
Cho et al.

(10) Patent No.: US 7,781,592 B2
(45) Date of Patent: Aug. 24, 2010

(54) THIONE DERIVATIVE, METHOD FOR THE PREPARATION THEREOF, AND PHARMACEUTICAL COMPOSITION CONTAINING THE SAME

(75) Inventors: Il Hwan Cho, Seoul (KR); Myeong Yun Chae, Sungnam (KR); Young Hoon Kim, Seoul (KR); Kyu Jeong Yeon, Yongin (KR); Chun Seon Lyu, Yongin (KR); Jong Hoon Kim, Anyang (KR); Sung Hak Jung, Seoul (KR); Sang Wook Park, Suwon (KR); Hyung Chul Ryu, Yongin (KR); Ji Young Noh, Busan (KR); Hyun Jung Park, Jeonju (KR); Jie Eun Park, Wonju (KR); Young Mee Chung, Suwon (KR)

(73) Assignee: CJ Cheiljedang Corporation, Seoul (KR)

( * ) Notice: Subject to any disclaimer, the term of this patent is extended or adjusted under 35 U.S.C. 154(b) by 952 days.

(21) Appl. No.: 10/580,454

(22) PCT Filed: Nov. 25, 2003

(86) PCT No.: PCT/KR03/02553

§ 371 (c)(1),
(2), (4) Date: May 24, 2006

(87) PCT Pub. No.: WO2005/051941

PCT Pub. Date: Jun. 9, 2005

(65) Prior Publication Data

US 2008/0090875 A1    Apr. 17, 2008

(51) Int. Cl.
*C07D 339/02* (2006.01)
*C07D 411/10* (2006.01)
(52) U.S. Cl. .................... 546/280.7; 549/36
(58) Field of Classification Search .......... 514/336, 514/441; 546/280.7; 549/36
See application file for complete search history.

(56) References Cited

U.S. PATENT DOCUMENTS

| 4,760,078 A | 7/1988 | Yamamoto et al. |
| 5,466,823 A | 11/1995 | Talley et al. |
| 5,470,871 A | 11/1995 | Christen et al. |
| 5,633,272 A | 5/1997 | Talley et al. |

FOREIGN PATENT DOCUMENTS

KR    1020040042246 A    5/2004

OTHER PUBLICATIONS

Park et al., J. Kor. Pharm. Sci. (Yakche Hakhoechi), (Jun. 2003), vol. 33(2), pp. 105-112. (abstract).*
Bruno Battistini, et al., "Cox-1 and Cox-2: Toward the Development of More Selective NSAIDs", Drug News and Perspectives, Oct. 1994, pp. 501-512, vol. 7.
Alexander Kirschenbaum, et al., "The Role of Cyclooxygenase-2 in Prostate Cancer", Urology, 2001, pp. 127-131, vol. 58 (Supplement 2A), Elsevier Science Inc.
Jeong-Ran Park, et al., "Screening of Anticancer Potential of Celecoxib and its Derivatives", J. Kor. Pharm. Sci., 2003, pp. 105-112, vol. 33.
David B. Reitz, et al., "Selective Cyclooxygenase Inhibitors", Annual Reports in Medicinal Chemistry, 1995, pp. 179-188, vol. 30, Academic Press, Inc.
D.J. Schrier, et al., "The pharmacologic effects of 5-[3,5-BIS(1,1-dimethylethyl)-4-hydroxyphenyl]-1,3,4-thiadiazole-2 (3H)-thione, choline salt (CI-986), a novel inhibitor of arachidonic acid metabolism in models of inflammation, analgesia and gastric irritation", Prostaglandins, 1994, pp. 17-30, vol. 47(1), Butterworth-Heinemann.
John Vane, "Towards a Better Aspirin", Nature, 1994, pp. 215-216, vol. 367, Nature Publishing Group.

* cited by examiner

*Primary Examiner*—Taofiq A Solola
(74) *Attorney, Agent, or Firm*—Rothwell, Figg, Ernst & Manbeck, pc

(57) ABSTRACT

A 1,2,4-triazole derivative of formula 1 or a non-toxic salt thereof, a preparation method thereof, and a pharmaceutical composition containing the derivative or the salt as an active ingredient are provided.

6 Claims, No Drawings

THIONE DERIVATIVE, METHOD FOR THE PREPARATION THEREOF, AND PHARMACEUTICAL COMPOSITION CONTAINING THE SAME

CROSS REFERENCE TO RELATED APPLICATION

This application is a 35 U.S.C. §371 National Phase Entry Application from PCT/KR2003/002553, filed Nov. 25, 2003, and designating the U.S.

BACKGROUND OF THE INVENTION

1. Field of the Invention

The present invention relates to a thione derivative or a non-toxic salt thereof which is effective in reduce inflammation, pain, or fever, a method for preparing the same, and a pharmaceutical composition containing the same as an active ingredient.

2. Description of the Related Art

Most nonsteroidal antiinflammatory agents are responsible for blocking enzyme, cyclooxygenase (COX) or prostaglandin G/H synthase, to reduce inflammation, pain, or fever. In addition, they inhibit uterus contraction caused by hormones and also inhibit growth of several cancers. Cyclooxygenase-1 (COX-1) was first discovered in bovine. The COX-1 is constitutively expressed in a variety of cell types. Unlike the COX-1, cyclooxygenase-2 (COX-2) is a recently discovered isoform of cyclooxygenase that can be easily induced by mitogen, endotoxin, hormone, growth factor, or cytokine.

Prostaglandin is a potent mediator for various pathological and physiological processes. The COX-1 plays important physiological roles such as in the release of endogenous prostaglandin, the maintenance of the shape and the function of stomach, and the blood circulation in the kidney. On the other hand, the COX-2 is induced by an inflammatory factor, hormone, a growth factor, or cytokine. Therefore, the COX-2 is involved in pathological processes of prostaglandin, unlike the constitutive COX-1. In this regard, selective inhibitors of the COX-2 produce fewer and less side effects in terms of action mechanism in comparison with conventional nonsteroidal antiinflammatory agents. In addition, they reduce inflammation, pain, and fever and inhibit uterus contraction caused by hormones and growth of several cancers. In particular, they are effective in decreasing side effects such as stomach toxicity and kidney toxicity. Still furthermore, they inhibit the synthesis of contractile prostanoid, thereby leading to suppression of the contraction of smooth muscles. Therefore, they help in preventing premature birth, menstrual irregularity, asthma, and eosinophilic disease.

In addition, it is anticipated that selective inhibitors of the COX-2 would be effective in treating osteoporosis and glaucoma. Utility of selective inhibitors of the COX-2 is well described in publications [John Vane, "Towards a Better Aspirin" in Nature, Vol. 367, pp 215-216, 1994; Bruno Battistini, Regina Botting and Y. S. Bakhle, "COX-1 and COX-2: Toward the Development of More Selective NSAIDs" in Drug News and Perspectives, Vol. 7, pp 501-512, 1994; Urology, Vol. 58, pp 127, 2001; David B. Reitz and Karen Seibert, "Selective Cyclooxygenase Inhibitors" in Annual Reports in Medicinal Chemistry, James A. Bristol, Editor, Vol. 30, pp 179-188, 1995].

Various selective COX-2 inhibitors having different structures are known. Among them, a selective COX-2 inhibitor having a diaryl heterocyclic structure, i.e. a tricyclic structure has been widely studied as a potent candidate. The diaryl heterocyclic structure has a central ring and a sulfonamide or methylsulfone group attached to one of the aryl rings.

One selective COX-2 inhibitor, Celecoxib of formula 87 is disclosed in U.S. Pat. No. 5,466,823. The Celecoxib is a substituted pyrazolyl benzenesulfonamide derivative.

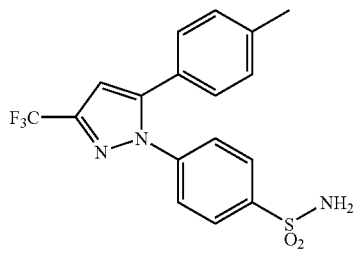

Formula 87

Another selective COX-2 inhibitor, Rofecoxib of formula 88 is disclosed in WO 95/00501. The Rofecoxib has a diaryl heterocyclic structure with a central furanone ring.

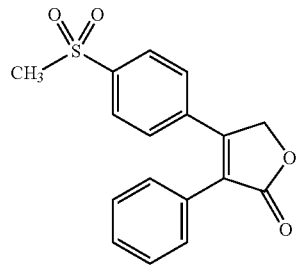

Formula 88

Valdecoxib of formula 89 as another selective COX-2 inhibitor is disclosed in U.S. Pat. No. 5,633,272. The Valdecoxib has a phenylsulfonamide moiety with a central isoxazole ring.

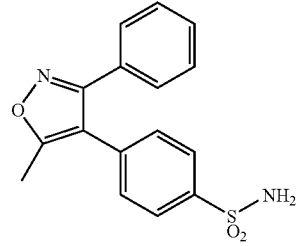

Formula 89

The selective COX-2 inhibitors of formulas 87 to 89 are effective inflammatory therapeutic agents with fewer and less side effects in comparison with conventional nonsteroidal antiinflammatory agents.

SUMMARY OF THE INVENTION

An aspect of the present invention provides a thione derivative of formula 1 or a non-toxic salt thereof.

Another aspect of the present invention provides a method for preparing a thione derivative or a non-toxic salt thereof.

Another aspect of the present invention provides a pharmaceutical composition comprising a thione derivative or a non-toxic salt thereof as an active ingredient for the treatment of fever, pain, and inflammation.

DETAILED DESCRIPTION OF THE INVENTION

According to an aspect of the present invention, there is provided a thione derivative represented by formula 1:

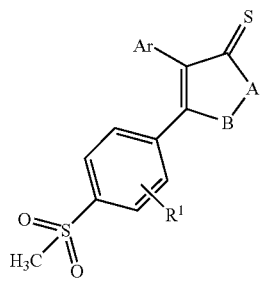

Formula 1 wherein:

A and B each independently represent O, S, $NR^2$; wherein $R^2$ represents hydrogen, $C_1$-$C_4$ alkyl, $C_1$-$C_4$ alkenyl, or aryl;

Ar represents aryl; heteroaryl; aryl or heteroaryl substituted with one to five radicals independently selected from the group consisting of $C_1$-$C_4$ alkyl, $C_1$-$C_4$ alkoxy, halogen, trifluoromethyl, nitro, acetoxy, amino, $C_1$-$C_3$ alkylamino, $C_1$-$C_3$ dialkylamino, hydroxy, $C_1$-$C_3$ hydroxyalkyl, and thioxy; and $R^1$ represents hydrogen, $C_1$-$C_4$ alkyl, $C_1$-$C_4$ alkoxy, halogen, cyano, nitro, hydroxy, amino, $C_1$-$C_4$ alkylamino, or $C_1$-$C_4$ dialkylamino;

or a non-toxic salt thereof.

Preferably, A and B each independently represent S or NH;

Ar represents phenyl; phenyl substituted with one to five radicals independently selected from the group consisting of $C_1$-$C_4$ alkyl, $C_1$-$C_4$ alkoxy, halogen, trifluoromethyl, acetoxy, and nitro; pyridyl; or naphthyl; and $R^1$ represents hydrogen or halogen.

The thione derivative of formula 1 may be present in a form of a non-toxic salt. The term, "non-toxic salt" as used herein refers to a pharmaceutically acceptable, toxin-free salt, including an organic salt and an inorganic salt.

The thione derivative of formula 1 may be present in a form of an organic acid salt or an inorganic acid salt.

Examples of the organic acid salt or the inorganic acid salt of the thione derivative of formula 1 include, but are not limited to, a salt of acetic acid, adipic acid, aspartic acid, 1,5-naphthalene disulfonic acid, benzene sulfonic acid, benzoic acid, camphor sulfonic acid, citric acid, 1,2-ethane disulfonic acid, ethane sulfonic acid, ethylenediaminetetraacetic acid, fumaric acid, glucoheptonic acid, gluconic acid, glutamic acid, hydroiodic acid, hydrobromic acid, hydrochloric acid, icethionic acid, lactic acid, maleic acid, malic acid, madelic acid, methane sulfonic acid, mucinic acid, 2-naphthalenedisulfonic acid, nitric acid, oxalic acid, pentothenic acid, phosphoric acid, pivalric acid, propionic acid, salicylic acid, stearic acid, succinic acid, sulfuric acid, tartaric acid, p-toluene sulfonic acid, undecanoic acid, and 10-undecenoic acid. Preferably, a salt of succinic acid, hydrobromic acid, hydrochloric acid, maleic acid, methanesulfonic acid, phosphoric acid, sulfuric acid, or tartaric acid is used.

The thione derivative of the present invention preferably includes:

4-(4-ethoxyphenyl)-5-(4-methanesulfonylphenyl)-[1,2] dithiol-3-thione;

4-(4-bromophenyl)-5-(4-methanesulfonylphenyl)-[1,2] dithiol-3-thione;

5-(4-methanesulfonylphenyl)-4-toryl-[1,2]dithiol-3-thione;

5-(4-methanesulfonylphenyl)-4-phenyl-[1,2]dithiol-3-thione;

5-(4-methanesulfonylphenyl)-4-methoxyphenyl-[1,2] dithiol-3-thione;

5-(4-methanesulfonylphenyl)-4-(2-trifluoromethylphenyl)-[1,2]dithiol-3-thione;

4-(4-chlorophenyl)-5-(4-methanesulfonylphenyl)-[1,2] dithiol-3-thione;

4-(3,4-dichlorophenyl)-5-(4-methanesulfonylphenyl)-[1,2] dithiol-3-thione;

5-(4-methanesulfonylphenyl)-4-pyridine-4-yl-[1,2]dithiol-3-thione;

5-(4-methanesulfonylphenyl)-4-pyridine-3-yl-[1,2]dithiol-3-thione;

5-(4-methanesulfonylphenyl)-4-pyridine-2-yl-[1,2]dithiol-3-thione;

4-(4-fluorophenyl)-5-(4-methanesulfonylphenyl)-[1,2] dithiol-3-thione;

4-(2,5-dimethoxyphenyl)-5-(4-methanesulfonylphenyl)-[1,2]dithiol-3-thione;

4-(3,5-dimethylphenyl)-5-(4-methanesulfonylphenyl)-[1,2] dithiol-3-thione;

5-(4-methanesulfonylphenyl)-4-(3-methoxyphenyl)-[1,2] dithiol-3-thione;

5-(4-methanesulfonylphenyl)-4-(2-nitrophenyl)-[1,2] dithiol-3-thione;

5-(4-methanesulfonylphenyl)-4-(3-trifluoromethylphenyl)-[1,2]dithiol-3-thione;

5-(4-methanesulfonylphenyl)-4-o-toryl-[1,2]dithiol-3-thione;

4-(2-chlorophenyl)-5-(4-methanesulfonylphenyl)-[1,2] dithiol-3-thione;

4-(2,4-dichlorophenyl)-5-(4-methanesulfonylphenyl)-[1,2] dithiol-3-thione;

4-(2-chloro-4-fluorophenyl)-5-(4-methanesulfonylphenyl)-[1,2]dithiol-3-thione;

4-(3,4-dimethoxyphenyl)-5-(4-methanesulfonylphenyl)-[1,2]dithiol-3-thione;

4-(2-bromophenyl)-5-(4-methanesulfonylphenyl)-[1,2] dithiol-3-thione;

4-(2-fluorophenyl)-5-(4-methanesulfonylphenyl)-[1,2] dithiol-3-thione;

4-(2,4-difluorophenyl)-5-(4-methanesulfonylphenyl)-[1,2] dithiol-3-thione;

4-(3,4-difluorophenyl)-5-(4-methanesulfonylphenyl)-[1,2] dithiol-3-thione;

5-(4-methanesulfonylphenyl)-4-naphthalene-2-yl-[1,2] dithiol-3-thione;

5-(4-methanesulfonylphenyl)-4-pentafluorophenyl-[1,2] dithiol-3-thione;

4-(4-isopropoxylphenyl)-5-(4-methanesulfonylphenyl)-[1, 2]dithiol-3-thione;

5-(4-methanesulfonylphenyl)-4-(4-propoxyphenyl)-[1,2] dithiol-3-thione; acetic acid 4-[5-(4-methanesulfonylphenyl)-3-thioxo-3H-[1,2]dithiol-4-yl]phenyl ester;

5-(2-chloro-4-methanesulfonylphenyl)-4-(4-ethoxyphenyl)-[1,2]dithiol-3-thione;

5-(2-chloro-4-methanesulfonylphenyl)-4-p-toryl-[1,2] dithiol-3-thione;

4-(4-bromophenyl)-5-(2-chloro-4-methanesulfonylphenyl)-[1,2]dithiol-3-thione;

5-(2-chloro-4-methanesulfonylphenyl)-4-(4-methoxyphenyl)-[1,2]dithiol-3-thione;

5-(3-fluoro-4-methanesulfonylphenyl)-4-p-toryl-[1,2]
  dithiol-3-thione;
5-(3-fluoro-4-methanesulfonylphenyl)-4-(4-methoxyphe-
  nyl)-[1,2]dithiol-3-thione;
acetic acid 4-[5-(3-fluoro-4-methanesulfonylphenyl)-3-
  thioxo-3H-[1,2]dithiol-4-yl]-phenyl ester;
5-(4-methanesulfonylphenyl)-4-p-toryl-1,2-dihydropyra-
  zole-3-thione;
4-(3,4-dichlorophenyl)-5-(4-methanesulfonylphenyl)-1,2-
  dihydropyrazole-3-thione; and
4-(4-chlorophenyl)-5-(4-methanesulfonylphenyl-1,2-dihy-
  dropyrazole-3-thione.

According to another aspect of the present invention, there is provided a propionic acid derivative as an intermediate for the synthesis of the thione derivative of formula 1, as represented by formula 2:

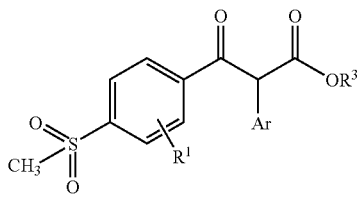

Formula 2 wherein, $R^1$ and Ar are as defined in formula 1 and $R^3$ represents $C_1$-$C_4$ alkyl.

According to another aspect of the present invention, there is provided A method for preparing a thione derivative of formula 1a or a non-toxic salt thereof, comprising reacting a propionic acid derivative of formula 2 with phosphorus pentasulfide, Lawesson's Reagent, beta-oxothioctic acid, or potassium beta-oxothioctate:

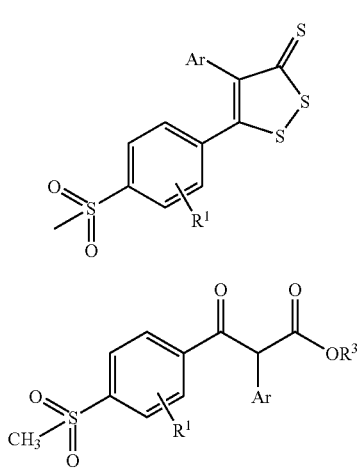

Formula 1a

Formula 2 wherein:
$R^1$ and Ar are as defined in claim 1;
$R^3$ represents $C_1$-$C_3$ alkyl.

Among phosphorus pentasulfide, Lawesson's Reagent, beta-oxothioctic acid, or potassium beta-oxothioctate, which is used to introduce thione structure, phosphorus pentasulfide is most preferred.

The said reaction is commonly carried out in an unreactive organic solvent, which includes but is not limited to benzene, toluene, and xylene. Among them, toluene is most preferred.

The said reactions may be completed by heating the solvent to its boiling point. For example, when toluene is used as a solvent, the reaction may be completed by heating toluene to the boiling point and refluxing it.

The above propionic acid derivative of formula 2 may be prepared by reacting a methanesulfonylbenzoic acid derivative of formula 3 with a aryl acetate derivative of formula 4 in the presence of a base;

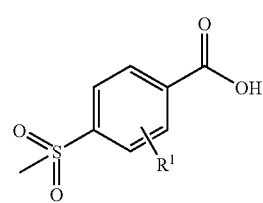

Formula 3

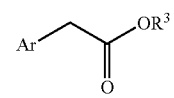

Formula 4 wherein, $R^1$ and Ar are as defined in formula 1 and $R^3$ represents $C_1$-$C_4$ alkyl.

The said base includes, but is not limited to sodium hydride, potassium carbonate, or potassium hydroxide. Preferably, sodium hydride is used.

According to another aspect of the present invention, there is provided a method for preparing a thione derivative of formula 1b or a non-toxic salt thereof, comprising reacting a thione derivative of formula 1a with $NHR^2NHR^2$ or $NHR^2OH$ in the presence of a base:

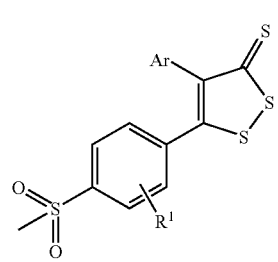

Formula 1a

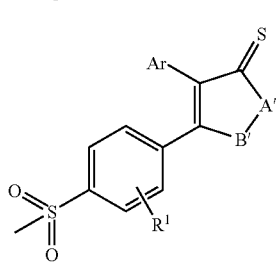

Formula 1b wherein, A' and B' each independently represent S or $NR^2$, provided that A' and B' are not simultaneously S; and Ar and $R^2$ are as defined in formula 1.

The said base includes, but is not limited to calcium carbonate, potassium hydroxide, or sodium hydroxide. Preferably, potassium hydroxide is used.

The separation and purification of the reaction products can be performed by concentration, extraction, or other processes, which is conventionally used in organic synthesis process, and optionally by a silica gel column chromatography.

A preferred embodiment of the method for preparing a compound of formula 1a and formula 1b is expressed by the following scheme 1:

Reaction formula 1

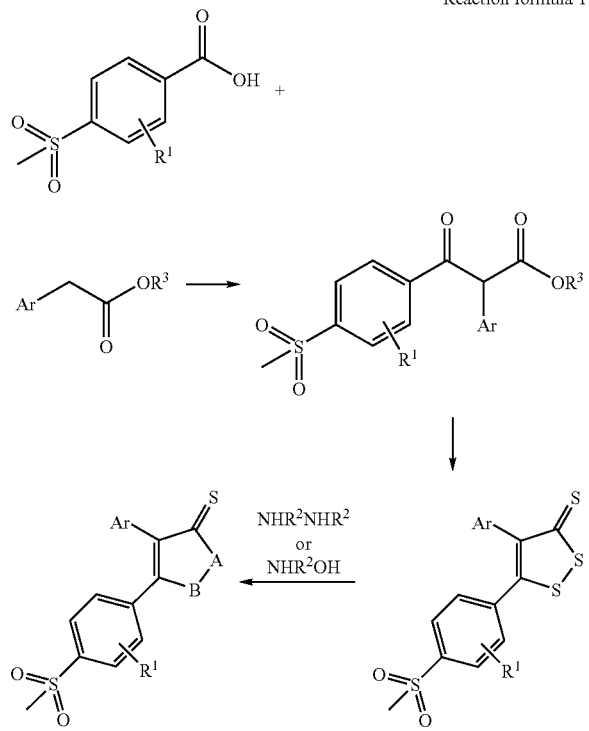

wherein, A, B, Ar, $R^1$, $R^2$, and $R^3$ are as defined in the above.

When $R^1$ is fluorine in the formula 1a of the present invention, the method for preparing a compound of the present invention may be expressed by the following scheme 2:

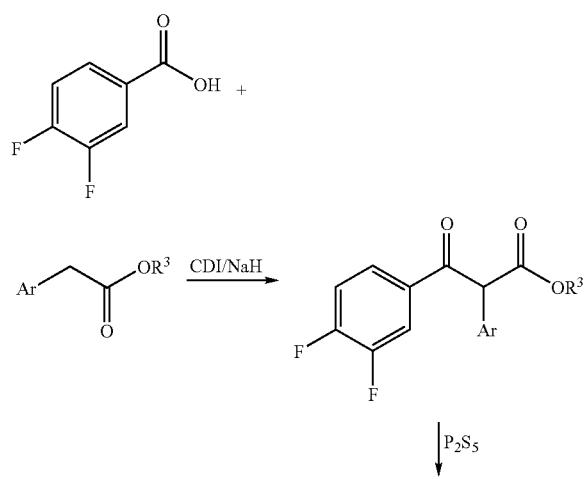

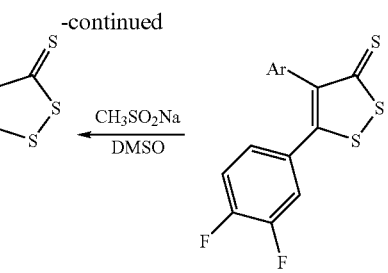

wherein, Ar and $R^3$ are as defined in the above.

According to another aspect of the present invention, there is provided a pharmaceutical composition comprising a therapeutically effective amount of a thione derivative of formula 1 or a non-toxic salt thereof as an active ingredient and a pharmaceutically acceptable carrier for treatment of fever, pain, and inflammation.

The pharmaceutical composition comprises a compound of formula 1 or a non-toxic salt thereof when it is a selective inhibitor of cyclooxygenase-2. Therefore, the pharmaceutical composition can be used as an antipyretic, an analgesic, and an antiinflammatory agent, with reduced side effects.

Conventional nonsteroidal antiinflammatory agents non-selectively inhibit the prostaglandin synthesis enzymes, cyclooxygenase-1 and cyclooxygenase-2. Therefore, various side effects may occur.

On the other hand, a compound of formula 1 and a non-toxic salt thereof selectively inhibit cyclooxygenase-2. Therefore, the side effects of conventional nonsteroidal antipyretics, analgesics, and antiinflammatory agents can be reduced.

The pharmaceutical composition of the present invention comprises a compound of formula 1 and/or a non-toxic salt thereof and a pharmaceutically acceptable carrier or excipient. Therefore, the pharmaceutical composition may be used as a substitute for conventional nonsteroidal antiinflammatory agents. In particular, due to the reduction of the side effects of conventional nonsteroidal antipyretics, analgesics, and antiinflammatory agents, the pharmaceutical composition of the present invention is useful in treating patients with peptic ulcer, gastritis, regional enteritis, ulcerative colitis, diverticullitis, gastrorrhagia, or hypoprothrombinemia.

The pharmaceutical composition of the present invention can be used in all inflammatory diseases associated with pathological prostaglandin and is particularly useful in treating osteoarthritis and rheumatoid arthritis which require high dosage of nonsteroidal antiinflammatory agents.

The pharmaceutical composition of the present invention can be administered in the form of an adult dosage of 1 mg/day to 1000 mg/day of the compound of formula 1. An adequate dosage is determined depending on the degree of disease severity.

The pharmaceutical composition of the present invention may be administered in the form of tablet, foam tablet, capsule, granule, powder, sustained-release tablet, sustained-release capsule (a single unit formulation or a multiple unit formulation), intravenous and intramuscular injectable solution, infusion solution, suspension, or suppository, or in other suitable dosage forms.

Sustained-release pharmaceutical dosage forms contain active ingredients with or without an initial loading dose. They are wholly or partially sustained-release pharmaceutical dosage forms to release active ingredients in a controlled manner.

Preferably, the pharmaceutical composition is orally administered.

The pharmaceutical composition further comprises a pharmaceutically acceptable excipient and/or diluent and/or adjuvant in pharmaceutically effective amounts.

Examples of the excipient and adjuvant include gellatin, a natural sugar such as sucrose and lactose, lecitin, pectin, starch such as corn starch and amylose, cyclodextrin and cyclodextrin derivative, dextran, polyvinylpyrrolidone, polyvinyl acetate, Arabic gum, arginic acid, xylose, talc, salicylic acid, calcium hydrogen phosphate, cellulose, cellulose derivative such as methylcellulose, methoxypropyl cellulose, hydroxypropylmethyl cellulose, and hydroxypropylmethylcellulose phthalate, fatty acid having 12 to 22 carbon atoms, emulsifying agent, oil and fat, in particular, vegetable glycerol ester and polyglycerol ester of saturated fatty acids, monohydric alcohol, polyhydric alcohol, polyglycol such as polyethylene glycol, aliphatic alcohol having 1 to 20 carbon atoms, or aliphatic saturated or unsaturated fatty acid ester having 2 to 22 carbon atoms with polyhydric alcohols such as glycol, glycerol, diethylene glycol, 1,2-propylene glycol, sorbitol, and mannitol.

Other suitable adjuvants include a disintegrating agent. Examples of the disintegrating agent include a cross-linked polyvinylpyrrolidone, sodium carboxymethyl starch, sodium carboxymethyl cellulose, and microcrystalline cellulose. A coating agent which is conventionally used in this field may also be used. Examples of the coating agent include acrylic acid and/or methacrylic acid and/or an ester polymer or copolymer thereof, zein, ethyl cellulose, ethyl cellulose succinate, and Shellac.

A plasticizer suitable for the coating agent is citric ester and tartaric ester, glycerol and glycerol ester, or polyethylene glycol with different chain lengths.

A liquid composition such as solution and suspension is formulated in water or a physiological acceptable organic solvent such as alcohol and aliphatic alcohol.

The liquid pharmaceutical composition may further comprise a preservative such as potassium solvate, methyl 4-hydroxybenzoate, and propyl 4-hydroxybenzoate, an antioxidant such as ascorbic acid, and a fragrant such as peppermint oil.

In addition, when the liquid pharmaceutical composition is formulated, a conventional solubilizer or emulsifier such as polyvinylpyrrolidone and polysolvate 80 may be used.

Other examples of suitable excipients and adjuvants are disclosed in Dr. H. P. Fielder, "Lexikon der Hilfsstoffe fur Pharmazie, Kosmetik und angrenzende Gebiete" [Encyclopaedia of auxiliaries for pharmacy, cosmetics and related fields].

Hereinafter, the present invention will be described more specifically by examples. However, the following examples are provided only for illustration and thus the present invention is not limited to or by them.

Example 1

2-(4-ethoxyphenyl)-3-(4-methanesulfonylphenyl)-oxo-propionic acid ethyl ester

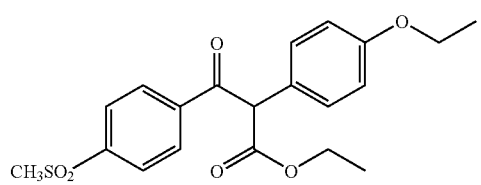

Formula 5

499 mg of 4-ethoxyphenylacetic acid ethyl ester, 480 mg of carbonyldiimidazole, and 0.5 g of 4-methanesulfonyl benzoic acid were dissolved in 10 ml of dimethy formamide, and 119 mg of sodium hydride were slowly added dropwise to the solution and the mixture was reacted at the room temperature for 12 hours. Afterwards, water was added to dilute the resultant, followed by extraction with ethyl acetate. The obtained organic layer was dried over anhydrous magnesium sulfate to give 0.9 g of the titled compound as a light yellow liquid (yield 92%).

$^1$H-NMR (400 MHz, CDCl$_3$) δ $^1$H-NMR (400 MHz, CDCl$_3$) δ 8.14 (d, 2H, J=8.4 Hz), 8.04 (d, 2H, J=8.4 Hz), 6.95 (d, 2H, J=8.4 Hz), 6.65 (d, 2H, J=8.4 Hz), 5.56 (s, 1H), 4.12 (q, 2H, J=6 Hz), 3.98 (q, 2H, J=6.0 Hz), 3.02 (s, 3H), 1.33-1.31 (m, 6H)

Example 2

2-(4-bromophenyl)-3-(4-methanesulfonylphenyl)-3-oxo-propionic acid ethyl ester

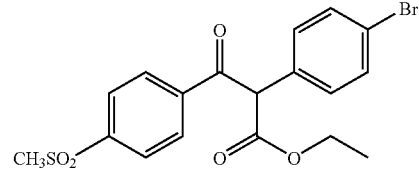

Formula 6

1.2 g (yield 89%) of the titled compound as a liquid was prepared in the same manner as in Example 1 except using 700 mg of 4-bromophenylacetic acid ethyl ester instead of 4-ethoxyphenylacetic acid ethyl ester.

$^1$H-NMR (400 MHz, CDCl$_3$) δ 8.15 (d, 2H, J=8.4 Hz), 8.05 (d, 2H, J=8.4 Hz), 6.97 (d, 2H, J=8.4 Hz), 6.94 (d, 2H, J=8.4 Hz), 5.55 (s, 1H), 4.12 (q, 2H, J=6 Hz), 3.02 (s, 3H), 1.33 (t, 3H, J=4.0 Hz)

Example 3

3-(4-methanesulfonyl)-3-oxo-2-p-toryl-propionic acid ethyl ester

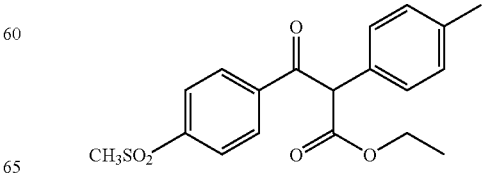

Formula 7

1.5 g (yield 83%) of the titled compound as a liquid was prepared in the same manner as in Example 1 except using 890 mg of p-torylacetic acid ethyl ester instead of 4-ethoxyphenylacetic acid ethyl ester.

$^1$H-NMR (400 MHz, CDCl$_3$) δ 8.14 (d, 2H, J=8.4 Hz), 8.03 (d, 2H, J=8.4 Hz), 6.96 (d, 2H, J=8.4 Hz), 6.93 (d, 2H, J=8.4 Hz), 5.56 (s, 1H), 4.12 (q, 2H, J=6 Hz), 3.02 (s, 3H), 2.33 (s, 2H), 1.33 (t, 3H, J=4.0 Hz)

Example 4

3-(4-methanesulfonylphenyl)-3-oxo-2-phenylpropionic acid methyl ester

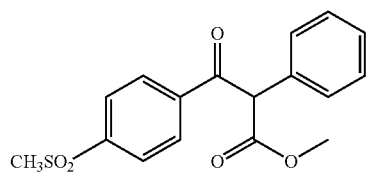

Formula 8

1.3 g (yield 80%) of the titled compound as a liquid was prepared in the same manner as in Example 1 except using 940 mg of phenylacetic acid methyl ester instead of 4-ethoxyphenylacetic acid ethyl ester.

$^1$H-NMR (400 MHz, CDCl$_3$) δ 8.15 (d, 2H, J=8.4 Hz), 8.05 (d, 2H, J=8.4 Hz), 6.97-6.94 (m, 5H), 5.56 (s, 1H), 3.75 (s, 3H), 3.02 (s, 3H)

Example 5

3-(4-methanesulfonylphenyl)-2-(4-methoxyphenyl)-3-oxo-propionic acid ethyl ester

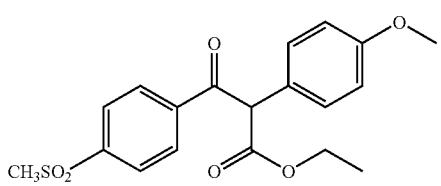

Formula 9

1.5 g (yield 83%) of the titled compound as a liquid was prepared in the same manner as in Example 1 except using 970 mg of 4-methoxyphenylacetic acid ethyl ester instead of 4-ethoxyphenylacetic acid ethyl ester.

$^1$H-NMR (400 MHz, CDCl$_3$) δ 8.15 (d, 2H, J=8.4 Hz), 8.05 (d, 2H, J=8.4 Hz), 6.96 (d, 2H, J=8.4 Hz), 6.93 (d, 2H, J=8.4 Hz), 5.56 (s, 1H), 4.12 (q, 2H, J=6.0 Hz), 3.79 (s, 3H), 3.02 (s, 3H), 1.33 (t, 3H, J=4.0 Hz)

Example 6

3-(4-methanesulfonylphenyl)-3-oxo-2-(2-trifluoromethylphenyl)-propionic acid ethyl ester

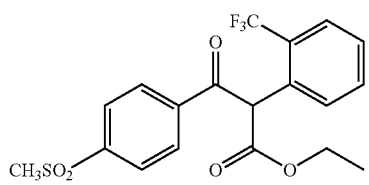

Formula 10

0.5 g (yield 65%) of the titled compound as a liquid was prepared in the same manner as in Example 1 except using 900 mg of 2-trifluoromethylphenylacetic acid ethyl ester instead of 4-ethoxyphenylacetic acid ethyl ester.

$^1$H-NMR (400 MHz, CDCl$_3$) δ 8.14 (d, 2H, J=8.4 Hz), 8.04 (d, 2H, J=8.4 Hz), 7.33 (d, 1H, J=6.8 Hz), 7.14 (t, 1H, J=6.0 Hz), 7.00-7.68 (m, 2H), 5.53 (s, 1H), 4.12 (q, 2H, J=6.0 Hz), 3.02 (S, 3H), 1.33 (t, 3H, J=4.0 Hz)

Example 7

2-(4-chlorophenyl)-3-(4-methanesulfonylphenyl)-3-oxo-propionic acid ethyl ester

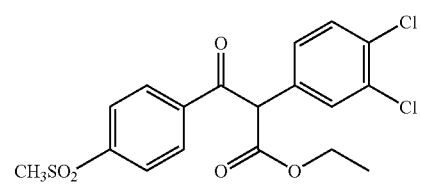

Formula 11

1.5 g (yield 78%) of the titled compound as a liquid was prepared in the same manner as in Example 1 except using 990 mg of 4-chlorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.96 (d, 2H, J=8.4 Hz), 6.92 (d, 2H, J=8.4 Hz), 5.55 (s, 1H), 4.12 (q, 2H, J=6.0 Hz), 3.02 (s, 3H), 1.33 (t, 3H, J=4.0 Hz)

Example 8

2-(3,4-dichlorophenyl)-3-(4-methanesulfonylphenyl)-3-oxo-propionic acid ethyl ester

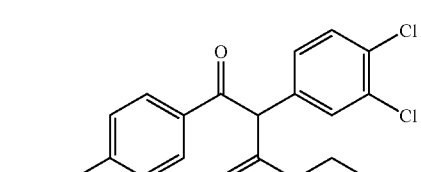

Formula 12

1.7 g (yield 85%) of the titled compound as a liquid was prepared in the same manner as in Example 1 except using 990 mg of 3,4-dichlorophenylacetic acid ethyl ester instead of 4-ethoxyphenylacetic acid ethyl ester.

$^1$H-NMR (400 MHz, CDCl$_3$) δ 8.14 (d, 2H, J=8.4 Hz), 8.04 (d, 2H, J=8.4 Hz), 7.09 (d, 1H, J=6.8 Hz), 7.01 (s, 1H), 6.88 (d, 1H, J=6.8 Hz), 5.53 (s, 1H), 4.12 (q, 2H, J=6.0 Hz), 3.02 (s, 3H), 1.33 (t, 3H, J=4.0 Hz)

Example 9

3-(4-methanesulfonylphenyl)-3-oxo-2-(pyridine-4-yl)-propionic acid ethyl ester

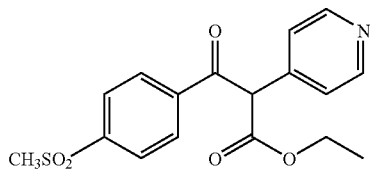

Formula 13

1.5 g (yield 78%) of the titled compound as a liquid was prepared in the same manner as in Example 1 except using 800 mg of pyridine-4-yl-acetic acid ethyl ester instead of 4-ethoxyphenylacetic acid ethyl ester.

$^1$H-NMR (400 MHz, CDCl$_3$) δ 8.55 (d, 2H, J=4.00 Hz), 7.85 (d, 2H, J=9.2 Hz), 7.39 (d, 2H, J=9.2 Hz), 6.99 (d, 2H, J=4.0 Hz), 5.50 (s, 1H), 4.12 (q, 2H, J=6.0 Hz), 3.02 (s, 3H), 1.33 (t, 3H, J=4.0 Hz)

Example 10

3-(4-methanesulfonylphenyl)-3-oxo-2-(pyridine-3-yl)-propionic acid ethyl ester

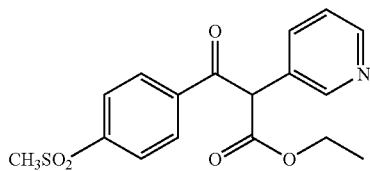

Formula 14

1.35 g (yield 78%) of the titled compound as a liquid was prepared in the same manner as in Example 1 except using 1 g of pyridine-3-yl-acetic acid ethyl ester instead of 4-ethoxyphenylacetic acid ethyl ester.

$^1$H-NMR (400 MHz, CDCl$_3$) δ 8.56 (s, 1H), 8.24 (d, 1H, J=4.0 Hz), 7.92 (d, 2H, J=8.0 Hz), 7.54 (d, 1H, J=4.0 Hz), 7.45 (d, 2H, J=8.0 Hz), 7.32 (t, 1H, J=6.0 Hz), 5.50 (s, 1H), 4.12 (q, 2H, J=6.0 Hz), 3.03 (s, 3H), 1.33 (t, 3H, J=4.0 Hz)

Example 11

3-(4-methanesulfonylphenyl)-3-oxo-2-(pyridine-2-yl)-propionic acid ethyl ester

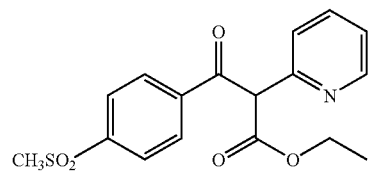

Formula 15

1.35 g (yield 78%) of the titled compound as a liquid was prepared in the same manner as in Example 1 except using 1 g of pyridine-2-yl-acetic acid ethyl ester instead of 4-ethoxyphenylacetic acid ethyl ester.

$^1$H-NMR (400 MHz, CDCl$_3$) δ 8.56 (d, 1H, J=6.8 Hz), 8.14 (d, 2H, J=8.4 Hz), 8.04 (d, 2H, J=8.4 Hz), 7.27-7.22 (m, 3H), 5.56 (s, 1H), 4.12 (q, 2H, J=6.0 Hz), 3.14 (s, 3H), 1.37 (t, 3H, J=4.0 Hz)

Example 12

2-(4-fluorophenyl)-3-(4-methanesulfonylphenyl)-3-oxo-propionic acid ethyl ester

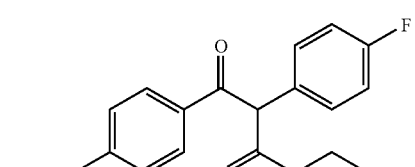

Formula 16

1.54 g (yield 85%) of the titled compound as a liquid was prepared in the same manner as in Example 1 except using 1 g of 4-fluorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 7.09-7.04 (m, 4H), 5.55 (s, 1H), 4.12 (q, 2H, J=6.0 Hz), 3.02 (s, 3H), 1.33 (t, 3H, J=4.0 Hz)

Example 13

2-(2,5-dimethoxyphenyl)-3-(4-methanesulfonylphenyl)-3-oxo-propionic acid ethyl ester

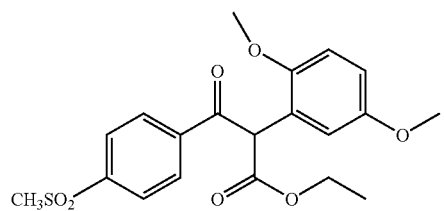

Formula 17

0.9 g (yield 90%) of the titled compound as a liquid was prepared in the same manner as in Example 1 except using 560 mg of 2,5-dimethoxyphenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.96 (d, 2H, J=8.4 Hz), 6.92 (d, 2H, J=8.4 Hz), 5.55 (s, 1H), 4.12 (q, 2H, J=6.0 Hz), 3.02 (s, 3H), 1.33 (t, 3H, J=4.0 Hz)

Example 14

2-(3,5-dimethylphenyl)-3-(4-methanesulfonylphenyl)-3-oxo-propionic acid ethyl ester Formula 18

810 mg (yield 88%) of the titled compound as a liquid was prepared in the same manner as in Example 1 except using 460 mg of 3,5-dimethylphenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.96 (d, 2H, J=8.4 Hz), 6.92 (d, 2H, J=8.4 Hz), 5.55 (s, 1H), 4.12 (q, 2H, J=6.0 Hz), 3.02 (s, 3H), 2.32 (s, 6H), 1.33 (t, 3H, J=4.0 Hz)

Example 15

3-(4-methanesulfonylphenyl)-2-(3-methoxyphenyl)-3-oxo-propionic acid ethyl ester Formula 19

860 mg (yield 92%) of the titled compound as a liquid was prepared in the same manner as in Example 1 except using 460 mg of 3-methoxyphenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 7.03 (t, 1H, J=4.2 Hz), 6.57-6.58 (m, 3H), 5.55 (s, 1H), 4.12 (q, 2H, J=6.0 Hz), 3.72 (s, 3H), 3.02 (s, 3H), 1.33 (t, 3H, J=4.0 Hz)

Example 16

3-(4-methanesulfonylphenyl)-2-(2-nitrophenyl)-3-oxo-propionic acid ethyl ester

Formula 20

830 mg (yield 85%) of the titled compound as a liquid was prepared in the same manner as in Example 1 except using 500 mg of 2-nitrophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.07 (d, 1H, J=6.4 Hz), 8.04 (t, 1H, J=4.2 Hz), 7.53-7.52 (m, 1H), 7.33-7.32 (m, 2H), 5.55 (s, 1H), 4.12 (q, 2H, J=6.0 Hz), 3.02 (s, 3H), 1.33 (t, 3H, J=4.0 Hz)

Example 17

3-(4-methanesulfonylphenyl)-3-oxo-2-(3-trifluoromethylphenyl)-propionic acid ethyl ester Formula 21

830 mg (yield 85%) of the titled compound as a liquid was prepared in the same manner as in Example 1 except using 500 mg of 3-trifluoromethylphenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 7.26-25 (m, 2H), 7.07-7.06 (m, 2H), 5.55 (s, 1H), 4.12 (q, 2H, J=6.0 Hz), 3.72 (s, 3H), 3.02 (s, 3H), 1.33 (t, 3H, J=4.0 Hz)

Example 18

3-(4-methanesulfonylphenyl)-3-oxo-2-o-toryl-propionic acid ethyl ester

Formula 22

820 mg (yield 91%) of the titled compound as a liquid was prepared in the same manner as in Example 1 except using 420 mg of o-torylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.95-6.93 (m, 4H), 5.55 (s, 1H), 4.12 (q, 2H, J=6.0 Hz), 3.02 (s, 3H), 2.35 (s, 3H), 1.33 (t, 3H, J=4.0 Hz)

Example 19

2-(2-chlorophenyl)-3-(4-methanesulfonylphenyl)-3-oxo-propionic acid ethyl ester

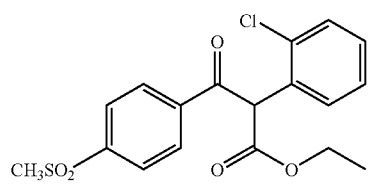

Formula 23

880 mg (yield 93%) of the titled compound as a liquid was prepared in the same manner as in Example 1 except using 490 mg of 2-chlorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.97-6.98 (m, 4H), 5.55 (s, 1H), 4.12 (q, 2H, J=6.0 Hz), 3.02 (s, 3H), 1.33 (t, 3H, J=4.0 Hz)

Example 20

2-(2,4-dichlorophenyl)-3-(4-methanesulfonylphenyl)-3-oxo-propionic acid ethyl ester

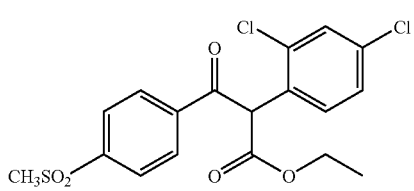

Formula 24

800 mg (yield 85%) of the titled compound as a liquid was prepared in the same manner as in Example 1 except using 470 mg of 2,4-dichlorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 7.16 (s, 1H), 7.03-7.01 (m, 2H), 5.55 (s, 1H), 4.12 (q, 2H, J=6.0 Hz), 3.02 (s, 3H), 1.33 (t, 3H, J=4.0 Hz)

Example 21

2-(2-chloro-4-fluorophenyl)-3-(4-methanesulfonylphenyl)-3-oxo-propionic acid ethyl ester

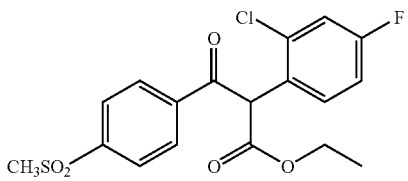

Formula 25

836 mg (yield 88%) of the titled compound as a liquid was prepared in the same manner as in Example 1 except using 520 mg of 2-chloro-4-fluorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.98 (t, 1H, J=6.0 Hz), 6.86 (d, 1H, J=5.6 Hz), 6.73 (d, 1H, J=5.6 Hz), 5.55 (s, 1H), 4.12 (q, 2H, J=6.0 Hz), 3.02 (s, 3H), 1.33 (t, 3H, J=4.0 Hz)

Example 22

2-(3,4-dimethoxyphenyl)-3-(4-methanesulfonylphenyl)-3-oxo-propionic acid ethyl ester

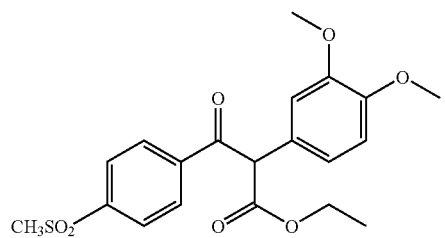

Formula 26

760 mg (yield 80%) of the titled compound as a liquid was prepared in the same manner as in Example 1 except using 560 mg of 3,4-dimethoxyphenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.53-6.51 (m, 2H), 6.46 (s, 1H), 5.55 (s, 1H), 4.12 (q, 2H, J=6.0 Hz), 3.73 (s, 6H), 3.02 (s, 3H), 1.33 (t, 3H, J=4.0 Hz)

Example 23

2-(2-bromophenyl)-3-(4-methanesulfonylphenyl)-3-oxo-propionic acid ethyl ester

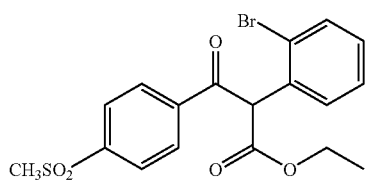

Formula 27

900 mg (yield 85%) of the titled compound as a liquid was prepared in the same manner as in Example 1 except using 660 mg of 2-bromophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.99-6.97 (m, 4H), 5.55 (s, 1H), 4.12 (q, 2H, J=6.0 Hz), 3.02 (s, 3H), 1.33 (t, 3H, J=4.0 Hz)

Example 24

2-(2-fluorophenyl)-3-(4-methanesulfonylphenyl)-3-oxo-propionic acid ethyl ester

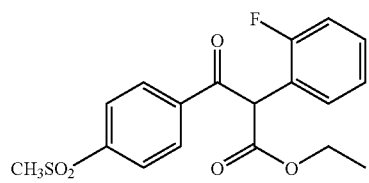

Formula 28

800 mg (yield 88%) of the titled compound as a liquid was prepared in the same manner as in Example 1 except using 440 mg of 2-fluorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 7.03-7.01 (m, 4H), 5.55 (s, 1H), 4.12 (q, 2H, J=6.0 Hz), 3.02 (s, 3H), 1.33 (t, 3H, J=4.0 Hz)

Example 25

2-(2,4-difluorophenyl)-3-(4-methanesulfonylphenyl)-3-oxo-propionic acid ethyl ester

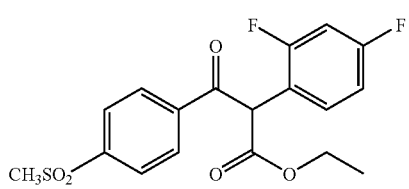

Formula 29

849 mg (yield 89%) of the titled compound as a liquid was prepared in the same manner as in Example 1 except using 480 mg of 2,4-difluorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 7.02-7.01 (m, 2H), 6.56 (m, 1H), 5.55 (s, 1H), 4.12 (q, 2H, J=6.0 Hz), 3.02 (s, 3H), 1.33 (t, 3H, J=4.0 Hz)

Example 26

2-(3,4-difluorophenyl)-3-(4-methanesulfonylphenyl)-3-oxo-propionic acid ethyl ester

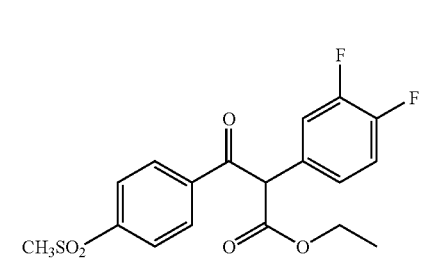

Formula 30

874 mg (yield 92%) of the titled compound as a liquid was prepared in the same manner as in Example 1 except using 480 mg of 3,4-difluorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 6.83-6.81 (m, 2H), 6.75 (m, 1H), 5.55 (s, 1H), 4.12 (q, 2H, J=6.0 Hz), 3.02 (s, 3H), 1.33 (t, 3H, J=4.0 Hz)

Example 27

3-(4-methanesulfonylphenyl)-2-(naphthalene-2-yl)-3-oxo-propionic acid ethyl ester

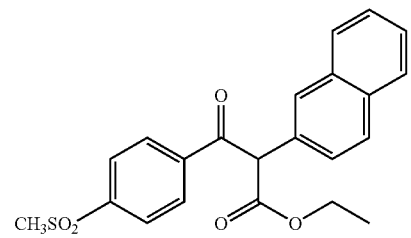

Formula 31

870 mg (yield 88%) of the titled compound as a liquid was prepared in the same manner as in Example 1 except using 530 mg of naphthalene-2-yl-acetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 7.68-7.64 (m, 3H), 7.46 (s, 1H), 7.31-7.30 (m, 2H), 7.16-7.15 (m, 1H), 5.55 (s, 1H), 4.12 (q, 2H, J=6.0 Hz), 3.02 (s, 3H), 1.33 (t, 3H, J=4.0 Hz)

Example 28

3-(4-methanesulfonylphenyl)-3-oxo-2-pentafluorophenyl-propionic acid ethyl ester

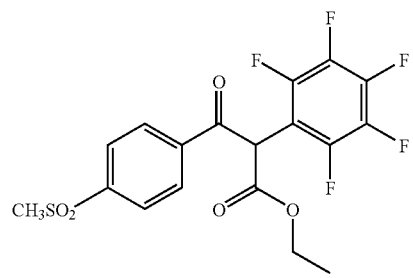

Formula 32

880 mg (yield 85%) of the titled compound as a liquid was prepared in the same manner as in Example 1 except using 550 mg of pentafluorophenylacetic acid ethyl ester instead of 4-ethoxyphenylacetic acid ethyl ester.

$^1$H-NMR (400 MHz, CDCl$_3$) δ 8.13 (d, 2H, J=8.4 Hz), 8.04 (d, 2H, J=8.4 Hz), 5.53 (s, 1H), 4.12 (q, 2H, J=6.0 Hz), 3.01 (s, 3H), 1.33 (t, 3H, J=4.0 Hz)

Example 29

2-(4-isopropoxyphenyl)-3-(4-methanesulfonylphenyl)-3-oxo-propionic acid ethyl ester

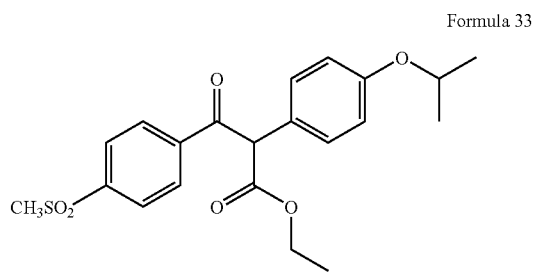

Formula 33

860 mg (yield 88%) of the titled compound as a liquid was prepared in the same manner as in Example 1 except using 500 mg of 4-isopropoxyphenylacetic acid ethyl ester instead of 4-ethoxyphenylacetic acid ethyl ester.

$^1$H-NMR (400 MHz, CDCl$_3$) δ 8.14 (d, 2H, J=8.4 Hz), 8.04 (d, 2H, J=8.4 Hz), 6.95 (d, 2H, J=8.4 Hz), 6.65 (d, 2H, J=8.4 Hz), 5.56 (s, 1H), 4.12 (q, 2H, J=6 Hz), 4.04-4.02 (m, 1H), 3.02 (s, 3H), 1.38 (s, 3H), 1.37 (s, 3H), 1.31 (t, 3H, J=4.0 Hz)

Example 30

3-(4-methanesulfonylphenyl)-3-oxo-2-(4-propoxyphenyl)-propionic acid ethyl ester

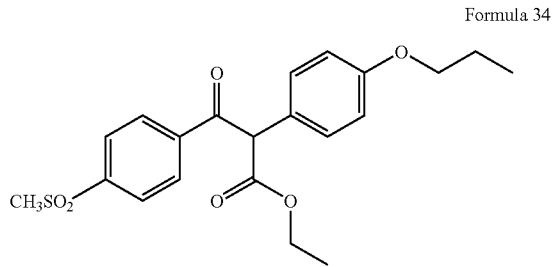

Formula 34

890 mg (yield 92%) of the titled compound as a liquid was prepared in the same manner as in Example 1 except using 500 mg of 4-propoxyphenylacetic acid ethyl ester instead of 4-ethoxyphenylacetic acid ethyl ester.

$^1$H-NMR (400 MHz, CDCl$_3$) δ 8.14 (d, 2H, J=8.4 Hz), 8.04 (d, 2H, J=8.4 Hz), 6.95 (d, 2H, J=−8.4 Hz), 6.65 (d, 2H, J=8.4 Hz), 5.56 (s, 1H), 4.12 (q, 2H, J=6 Hz), 3.94-3.95 (m, 2H), 3.02 (s, 3H), 1.75-1.74 (m, 2H), 1.30-1.28 (m, 6H)

Example 31

2-(4-acetoxyphenyl)-3-(4-methanesulfonylphenyl)-3-oxo-propionic acid ethyl ester

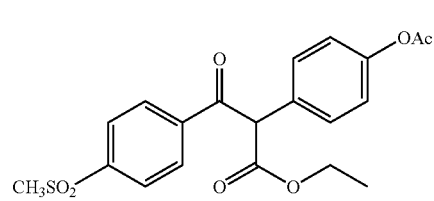

Formula 35

848 mg (yield 84%) of the titled compound as a liquid was prepared in the same manner as in Example 1 except using 500 mg of 4-aectoxyphenylacetic acid ethyl ester instead of 4-ethoxyphenylacetic acid ethyl ester.

$^1$H-NMR (400 MHz, CDCl$_3$) δ 8.14 (d, 2H, J=8.4 Hz), 8.04 (d, 2H, J=8.4 Hz), 7.03 (d, 2H, J=8.4 Hz), 6.95 (d, 2H, J=8.4 Hz), 5.56 (s, 1 h), 4.12 (q, 2H, J=6.0 Hz), 3.12 (s, 3H), 2.08 (s, 3H), 1.30 (t, 3H, J=4.0 Hz)

Example 32

3-(2-chloro-4-methanesulfonylphenyl)-2-(4-ethoxyphenyl)-3-oxo-propionic acid ethyl ester

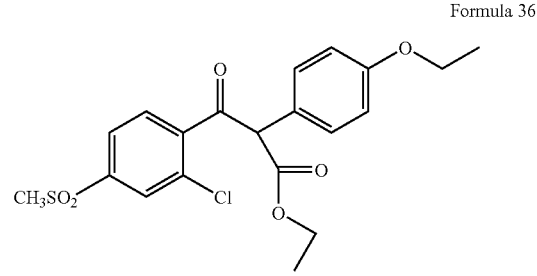

Formula 36

670 mg (yield 75%) of the titled compound as a liquid was prepared in the same manner as in Example 1 except using 500 mg of 2-chloro-4-methanesulfonylbenzoic acid instead of 4-methanesulfonylbenzoic acid.

$^1$H-NMR (400 MHz, CDCl$_3$) δ 8.08 (d, 1H, J=7.2 Hz), 8.05 (s, 1H), 7.92 (d, 1H, J=7.2 Hz), 6.95-6.94 (m, 4H), 5.56 (s, 1H), 4.12 (q, 2H, J=6 Hz), 3.98 (q, 2H, J=6.0 Hz), 3.02 (s, 3H), 1.33-1.31 (m, 6H)

Example 33

3-(2-chloro-4-methanesulfonylphenyl)-3-oxo-2-p-toryl-propionic acid ethyl ester

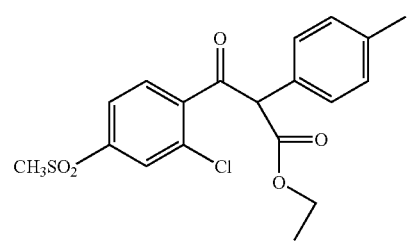

Formula 37

740 mg (yield 88%) of the titled compound as a liquid was prepared in the same manner as in Example 3 except using 500 mg of 2-chloro-4-methanesulfonylbenzoic acid instead of 4-methanesulfonylbenzoic acid.

$^1$H-NMR (400 MHz, CDCl$_3$) δ 8.08 (d, 1H, J=7.2 Hz), 8.05 (s, 1H), 7.92 (d, 1H, J=7.2 Hz), 6.95-6.94 (m, 4H), 5.56 (s, 1H), 4.12 (q, 2H, J=6 Hz), 3.02 (s, 3H), 2.35 (s, 3H), 1.33 (t, 3H, J=4.0 Hz)

Example 34

2-(4-bromophenyl)-3-(2-chloro-4-methanesulfonylphenyl)-3-oxo-propionic acid ethyl ester

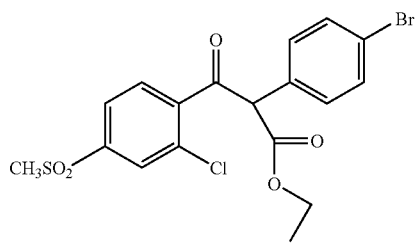

Formula 38

764 mg (yield 84%) of the titled compound as a liquid was prepared in the same manner as in Example 2 except using 500 mg of 2-chloro-4-methanesulfonylbenzoic acid instead of 4-methanesulfonylbenzoic acid.

$^1$H-NMR (400 MHz, CDCl$_3$) δ 8.08 (d, 1H, J=7.2 Hz), 8.05 (s, 1H), 7.92 (d, 1H, J=7.2 Hz), 6.98-6.97 (m, 4H), 5.55 (s, 1H), 4.13 (q, 2H, J=6 Hz), 3.02 (s, 3H), 1.33 (t, 3H, J=4.0 Hz)

Example 35

3-(2-chloro-4-methanesulfonylphenyl)-2-(4-methoxyphenyl)-3-oxo-propionic acid ethyl ester

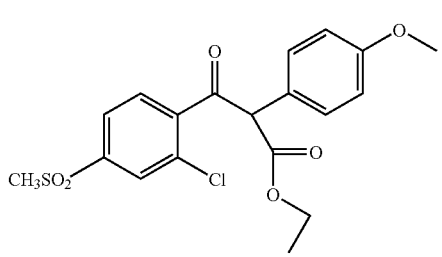

Formula 39

791 mg (yield 87%) of the titled compound as a liquid was prepared in the same manner as in Example 5 except using 500 mg of 2-chloro-4-methanesulfonylbenzoic acid instead of 4-methanesulfonylbenzoic acid.

$^1$H-NMR (400 MHz, CDCl$_3$) δ 8.08 (d, 1H, J=7.2 Hz), 8.05 (s, 1H), 7.92 (d, 1H, J=7.2 Hz), 6.95-6.94 (m, 4H), 5.56 (s, 1H), 4.13 (q, 2H, J=6 Hz), 3.75 (s, 3H), 3.02 (s, 3H), 1.33 (t, 3H, J=4.0 Hz)

Example 36

3-(3,4-difluorophenyl)-3-oxo-2-p-toryl-propionic acid ethyl ester

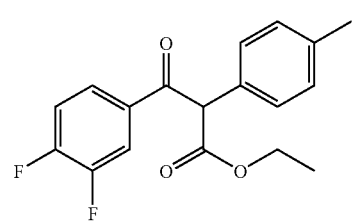

Formula 40

1.73 g (yield 82%) of the titled compound as a liquid was prepared in the same manner as in Example 3 except using 1 g of 3,4-difluorobenzoic acid instead of 4-methanesulfonylbenzoic acid.

$^1$H-NMR (400 MHz, CDCl$_3$) δ 7.17 (d, 2H, J=7.6 Hz), 7.05-7.03 (m, 3H), 6.99 (d, 2H, J=7.6 Hz), 5.52 (s, 1H), 4.12 (q, 2H, J=6.0 Hz), 2.35 (s, 3H), 1.30 (t, 3H, J=4.0 Hz)

Example 37

3-(3,4-difluorophenyl)-2-(4-methoxyphenyl)-3-oxo-propionic acid ethyl ester

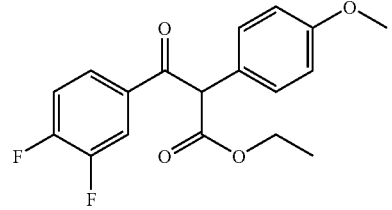

Formula 41

850 mg (yield 85%) of the titled compound as a liquid was prepared in the same manner as in Example 5 except using 500 mg of 3,4-difluorobenzoic acid instead of 4-methanesulfonylbenzoic acid.

$^1$H-NMR (400 MHz, CDCl$_3$) δ 7.16 (d, 2H, J=7.6 Hz), 7.04-7.02 (m, 3H), 6.99 (d, 2H, J=7.6 Hz), 5.52 (s, 1H), 4.12 (q, 2H, J=6.0 Hz), 3.82 (s, 3H), 1.30 (t, 3H, J=4.0 Hz)

Example 38

2-(4-acetoxyphenyl)-3-(3,4-difluorophenyl)-3-oxo-propionic acid ethyl ester

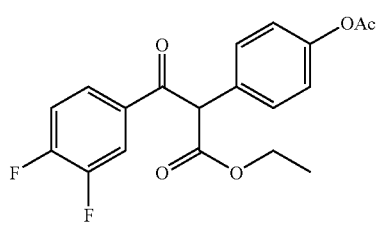

Formula 42

830 mg (yield 87%) of the titled compound as a liquid was prepared in the same manner as in Example 31 except using 416 mg of 3,4-difluorobenzoic acid instead of 4-methanesulfonylbenzoic acid.

$^1$H-NMR (400 MHz, CDCl$_3$) δ 7.17 (d, 2H, J=7.6 Hz), 7.05-7.03 (m, 3H), 6.99 (d, 2H, J=7.6 Hz), 5.52 (s, 1H), 4.12 (q, 2H, J=6.0 Hz), 2.32 (s, 3H), 1.30 (t, 3H, J=4.0 Hz)

Example 39

4-(4-ethoxyphenyl)-5-(4-methanesulfonylphenyl)-[1,2]dithiol-3-thione

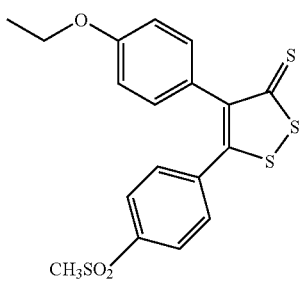

Formula 43

0.68 g of phosphorus pentasulfide was dissolved in 10 ml of toluene, and then 0.3 g of 2-(4-ethoxyphenyl)-3-(4-methanesulfonylphenyl)-3-oxo-propionic acid ethyl ester was added thereto to reflux for 4 hours at 110° C. Afterwards the reaction apparatus was cooled, and ammonia water was added thereto slowly to adjust pH 8 to 8.5. The reaction mixture was diluted with water and extracted with ethyl acetate. The obtained organic layer was dried on anhydrous magnesium sulfate to distill the solvent. The resultant was recrystallized with n-hexane to give 180 mg of the titled compound as a red solid (yield 60%).

$^1$H-NMR (400 MHz, CDCl$_3$) δ 7.88 (d, 2H, J=8.4 Hz), 7.45 (d, 2H, J=8.4 Hz), 7.01 (d, 2H, J=6.8 Hz), 6.85 (d, 2H, J=6.8 Hz), 4.02 (q, 2H, J=6.8 Hz), 3.05 (s, 3H), 1.42 (t, 3H, J=4.0 Hz)

EI Mass (M+): 408
Melting point: 210-212° C.

Example 40

4-(4-bromophenyl)-5-(4-methanesulfonylphenyl)-[1,2]dithiol-3-thione

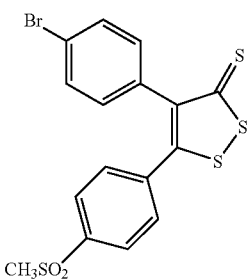

Formula 44

210 mg (yield 68%) of the titled compound as a liquid was prepared in the same manner as in Example 39 except using 0.3 g of 2-(4-bromophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (300 MHz, CDCl$_3$) δ 7.91 (d, 2H, J=8.4 Hz), 7.47 (d, 2H, J=8.4 Hz), 7.45 (d, 2H, J=8.4 Hz), 7.19 (d, 2H, J=8.4 Hz), 3.05 (s, 3H)

EI Mass (M+): 443
Melting point: 238-240° C.

Example 41

5-(4-methanesulfonylphenyl)-4-p-toryl-[1,2]dithiol-3-thione

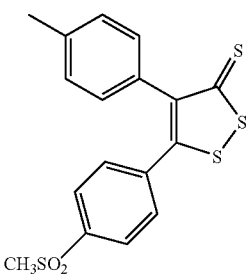

Formula 45

200 mg (yield 65%) of the titled compound as a liquid was prepared in the same manner as in Example 39 except using 0.3 g of 3-(4-methanesulfonylphenyl)-3-oxo-2-p-toryl-propionic acid ethyl ester instead of 2-(4-ethoxyphenyl)-3-(4-methanesulfonylphenyl)-3-oxo-propionic acid ethyl ester.

$^1$H-NMR (300 MHz, CDCl$_3$) δ 7.89 (d, 2H, J=9.0 Hz), 7.46 (d, 2H, J=9.0 Hz), 7.16 (d, 2H, J=9.0 Hz), 6.99 (d, 2H, J=9.0 Hz), 3.05 (s, 3H), 2.34 (s, 3H)

EI Mass (M+): 378
Melting point: 240-242° C.

Example 42

5-(4-methanesulfonylphenyl)-4-phenyl-[1,2]dithiol-3-thione

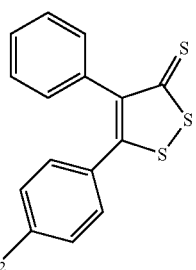

Formula 46

160 mg (yield 50%) of the titled compound as a liquid was prepared in the same manner as in Example 39 except using 0.3 g of 3-(4-methanesulfonylphenyl)-3-oxo-2-phenyl-propionic acid ethyl ester instead of 2-(4-ethoxyphenyl)-3-(4-methanesulfonylphenyl)-3-oxo-propionic acid ethyl ester.

¹H-NMR (300 MHz, CDCl₃) δ 7.87 (d, 2H, J=6.0 Hz), 7.44 (d, 2H, J=6.0 Hz), 7.35 (t, 3H, J=4.0 Hz), 7.12-7.10 (m, 2H), 3.04 (s, 3H)

EI Mass (M+): 364

Melting point: 200-202° C.

Example 43

5-(4-methanesulfonylphenyl)-4-(4-methoxyphenyl)-[1,2]dithiol-3-thione

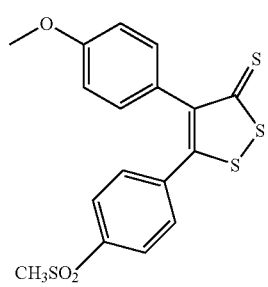

Formula 47

120 mg (yield 40%) of the titled compound as a liquid was prepared in the same manner as in Example 39 except using 0.3 g of 3-(4-methanesulfonylphenyl)-2-(4-methoxyphenyl)-3-oxo-propionic acid ethyl ester instead of 2-(4-ethoxyphenyl)-3-(4-methanesulfonylphenyl)-3-oxo-propionic acid ethyl ester.

¹H-NMR (300 MHz, CDCl₃) δ 7.90 (d, 2H, J=9.0 Hz), 7.46 (d, 2H, J=9.0 Hz), 7.04 (d, 2H, J=6.0 Hz), 6.88 (d, 2H, J=6.0 Hz), 3.81 (s, 3H), 3.05 (s, 3H)

EI Mass (M+): 394

Melting point: 220-222° C.

Example 44

5-(4-methanesulfonylphenyl)-4-(2-trifluoromethylphenyl)-[1,2]dithiol-3-thione

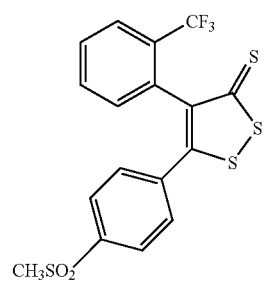

Formula 48

160 mg (yield 51%) of the titled compound as a liquid was prepared in the same manner as in Example 39 except using 0.3 g of 3-(4-methanesulfonylphenyl)-3-oxo-2-(2-trifluoromethylphenyl)-propionic acid ethyl ester instead of 2-(4-ethoxyphenyl)-3-(4-methanesulfonylphenyl)-3-oxo-propionic acid ethyl ester.

¹H-NMR (300 MHz, CDCl₃) δ 7.92 (d, 2H, J=6.0 Hz), 7.63 (d, 2H, J=6.0 Hz), 7.46 (d, 1H, J=9.0 Hz), 7.35 (d, 1H, J=9.0 Hz), 7.24-7.21 (m, 2H), 3.05 (s, 3H)

FAB Mass (M+1): 433

Melting point: 240-242° C.

Example 45

4-(4-chlorophenyl)-5-(4-methanesulfonylphenyl)-[1,2]dithiol-3-thione

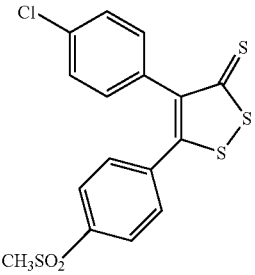

Formula 49

180 mg (yield 45%) of the titled compound as a liquid was prepared in the same manner as in Example 39 except using 0.4 g of 2-(4-chlorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

¹H-NMR (400 MHz, CDCl₃) δ 7.93 (d, 2H, J=8.0 Hz), 7.47 (d, 2H, J=8.0 Hz), 7.35 (d, 2H, J=8.0 Hz), 7.07 (d, 2H, J=8.0 Hz), 2.98 (s, 3H)

EI Mass (M+): 399

Melting point: 233-235° C.

Example 46

4-(3,4-dichlorophenyl)-5-(4-methanesulfonylphenyl)-[1,2]dithiol-3-thione

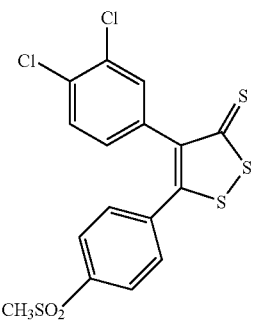

Formula 50

200 mg (yield 48%) of the titled compound as a liquid was prepared in the same manner as in Example 39 except using 0.4 g of 2-(3,4-dichlorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

¹H-NMR (400 MHz, CDCl₃) δ 7.98 (d, 2H, J=8.0 Hz), 7.49 (d, 2H, J=8.0 Hz), 7.44 (d, 1H, J=8.0 Hz), 7.35 (s, 1H), 7.07 (d, 1H, J=8.0 Hz), 3.09 (s, 3H)

EI Mass (M+) 443

Example 47

5-(4-methanesulfonylphenyl)-4-(pyridine-4-yl)-[1,2]dithiol-3-thione

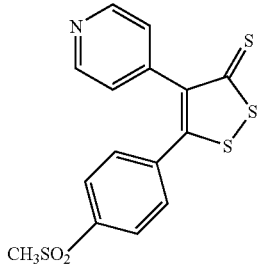

Formula 51

180 mg (yield 60%) of the titled compound as a liquid was prepared in the same manner as in Example 39 except using 0.3 g of 3-(4-methanesulfonylphenyl)-3-oxo-2-(pyridine-4-yl)-propionic acid ethyl ester instead of 2-(4-ethoxyphenyl)-3-(4-methanesulfonylphenyl)-3-oxo-propionic acid ethyl ester.

¹H-NMR (300 MHz, CDCl₃) δ 8.55 (d, 2H, J=4.0 Hz), 7.85 (d, 2H, J=9.2 Hz), 7.39 (d, 2H, J=9.2 Hz), 6.99 (d, 2H, J=4.0 Hz), 2.98 (s, 3H)

EI Mass (M+): 365

Melting point: 245-247° C.

Example 48

5-(4-methanesulfonylphenyl)-4-(pyridine-3-yl)-[1,2]dithiol-3-thione

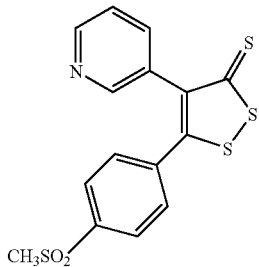

Formula 52

189 mg (yield 61%) of the titled compound as a liquid was prepared in the same manner as in Example 39 except using 0.3 g of 3-(4-methanesulfonylphenyl)-3-oxo-2-(pyridine-3-yl)-propionic acid ethyl ester instead of 2-(4-ethoxyphenyl)-3-(4-methanesulfonylphenyl)-3-oxo-propionic acid ethyl ester.

¹H-NMR (300 MHz, CDCl₃) δ 8.58 (s, 1H), 8.25 (d, 2H, J=4.0 Hz), 7.92 (d, 2H, J=8.0 Hz), 7.54 (d, 1H, J=4.0 Hz), 7.45 (d, 2H, J=8.0 Hz), 3.03 (s, 3H)

EI Mass (M+): 365

Example 49

5-(4-methanesulfonylphenyl)-4-(pyridine-2-yl)-[1,2]dithiol-3-thione

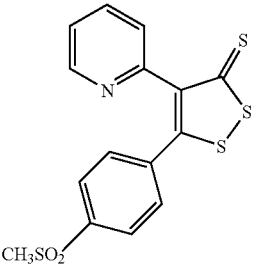

Formula 53

189 mg (yield 61%) of the titled compound as a liquid was prepared in the same manner as in Example 39 except using 0.3 g of 3-(4-methanesulfonylphenyl)-3-oxo-2-(pyridine-2-yl)-propionic acid ethyl ester instead of 2-(4-ethoxyphenyl)-3-(4-methanesulfonylphenyl)-3-oxo-propionic acid ethyl ester.

¹H-NMR (300 MHz, CDCl₃) δ 8.55 (m, 1H), 7.87 (dt, 2H, J=8.6 Hz, J=2.1 Hz), 7.75 (ddd, 1H, J=9.5 Hz, J=2.1 Hz, J=1.8 Hz), 7.50 (dt, 2H, J=8.6 Hz, J=2.1 Hz), 7.40 (dt, 1H, J=7.9 Hz, J=1.0 Hz), 7.26 (ddd, 1H, J=7.6 Hz, J=5.1 Hz, J=1.7 hZ), 3.04 (s, 3H)

EI Mass (M+): 365

Example 50

4-(4-fluorophenyl)-5-(4-methanesulfonylphenyl)-[1,2]dithiol-3-thione

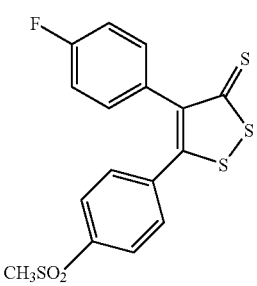

Formula 54

195 mg (yield 63%) of the titled compound as a liquid was prepared in the same manner as in Example 39 except using 0.3 g of 2-(4-fluorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

¹H-NMR (300 MHz, CDCl₃) δ 7.90 (d, 2H, J=8.0 Hz), 7.44 (d, 2H, J=8.0 Hz), 7.09-7.04 (m, 4H), 3.05 (s, 3H)

EI Mass (M+): 382

Melting point: 195-197° C.

Example 51

4-(2,5-dimethoxyphenyl)-5-(4-methanesulfonylphenyl)-[1,2]dithiol-3-thione

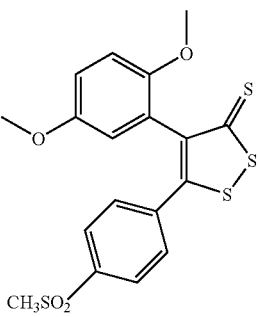

Formula 55

180 mg (yield 60%) of the titled compound as a liquid was prepared in the same manner as in Example 39 except using 0.3 g of 2-(2,5-dimethoxyphenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.87 (d, 2H, J=8.4 Hz), 7.51 (d, 2H, J=8.4 Hz), 6.87 (dd, 1H, J=12.0 Hz, J=2.8 Hz), 6.78 (d, 1H, J==12 Hz), 6.62 (d, 1H, J=2.8 Hz), 3.72 (s, 3H), 3.53 (s, 3H), 3.03 (s, 3H)

EI Mass (M+): 424

Melting point: 176-177° C.

Example 52

4-(3,5-dimethylphenyl)-5-(4-methanesulfonylphenyl)-[1,2]dithiol-3-thione

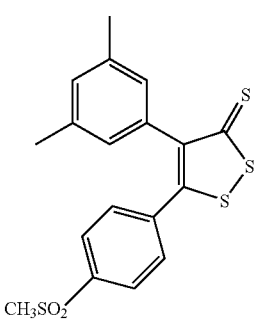

Formula 56

210 mg (yield 66%) of the titled compound as a liquid was prepared in the same manner as in Example 39 except using 0.3 g of 2-(3,5-dimethylphenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.88 (d, 2H, J=8.4 Hz), 7.47 (d, 2H, J=8.4 Hz), 6.96 (s, 1H), 6.69 (s, 2H), 3.03 (s, 3H), 2.37 (s, 6H)

EI Mass (M+): 392

Melting point: 164-165° C.

Example 53

5-(4-methanesulfonylphenyl)-4-(3-methoxyphenyl)-[1,2]dithiol-3-thione

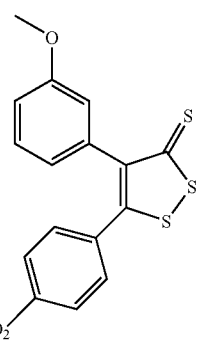

Formula 57

210 mg (yield 66%) of the titled compound as a liquid was prepared in the same manner as in Example 39 except using 0.3 g of 3-(4-methanesulfonylphenyl)-2-(3-methoxyphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.89 (d, 2H, J=8.4 Hz), 7.49 (d, 2H, J=8.4 Hz), 7.24 (t, 1H, J=8.2 Hz), 6.88 (d, 1H, J=7.2 Hz), 6.69 (s, 1H), 6.65 (d, 1H, J=7.2 Hz), 3.71 (s, 3H), 3.04 (s, 3H)

EI Mass (M+): 394

Melting point: 212-213° C.

Example 54

5-(4-methanesulfonylphenyl)-4-(2-nitrophenyl)-[1,2]dithiol-3-thione

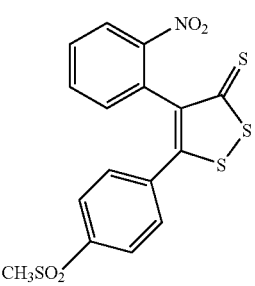

Formula 58

217 mg (yield 70%) of the titled compound as a liquid was prepared in the same manner as in Example 39 except using 0.3 g of 3-(4-methanesulfonylphenyl)-2-(2-nitrophenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 8.13 (d, 1H, J=6.8 Hz), 7.89 (d, 2H, J=8.4 Hz), 7.56-7.54 (m, 4H), 7.01 (d, 1H, J=6.8 Hz), 3.04 (s, 3H)

EI Mass (M+): 409

Melting point: 170-171° C.

Example 55

5-(4-methanesulfonylphenyl)-4-(3-trifluoromethylphenyl)-[1,2]dithiol-3-thione

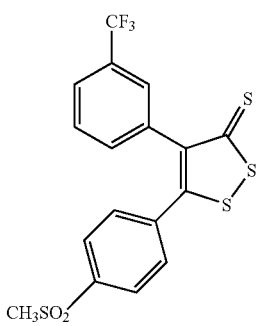

Formula 59

240 mg (yield 78%) of the titled compound as a liquid was prepared in the same manner as in Example 39 except using 0.3 g of 3-(4-methanesulfonylphenyl)-3-oxo-2-(3-trifluoromethylphenyl)-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.90 (d, 2H, J=8.4 Hz), 7.59 (d, 1H, J=7.6 Hz), 7.49 (t, 1H, J=8.0 Hz), 7.43 (d, 2H, J=8.4 Hz), 7.38 (d, 1H, J=7.6 Hz), 7.29 (s, 1H), 3.04 (s, 3H)

EI Mass (M+): 432

Melting point: 188-189° C.

Example 56

5-(4-methanesulfonylphenyl)-4-o-toryl-[1,2]dithiol-3-thione

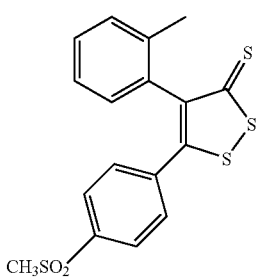

Formula 60

173 mg (yield 56%) of the titled compound as a liquid was prepared in the same manner as in Example 39 except using 0.3 g of 3-(4-methanesulfonylphenyl)-3-oxo-2-o-toryl-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.87 (d, 2H, J=8.4 Hz), 7.46 (d, 2H, J=8.4 Hz), 7.30 (d, 1H, J=7.6 Hz), 7.22-7.17 (m, 2H), 6.96 (d, 1H, J=7.6 Hz), 3.04 (s, 3H), 2.10 (s, 3H)

EI Mass (M+): 378

Melting point: 165-166° C.

Example 57

4-(2-chlorophenyl)-5-(4-methanesulfonylphenyl)-[1,2]dithiol-3-thione

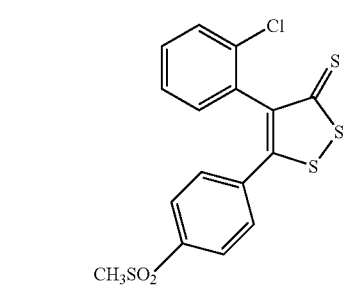

Formula 61

210 mg (yield 68%) of the titled compound as a liquid was prepared in the same manner as in Example 39 except using 0.3 g of 2-(2-chlorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.90 (d, 2H, J=8.4 Hz), 7.53 (d, 2H, J=8.4 Hz), 7.43 (dd, 1H, J=9.2 Hz, J=1.6 Hz), 7.32 (m, 2H), 7.12 (dd, 1H, J=9.2 Hz, J=1.6 Hz), 3.05 (s, 3H)

EI Mass (M+): 398

Melting point: 161-162° C.

Example 58

4-(2,4-dichlorophenyl)-5-(4-methanesulfonylphenyl)-[1,2]dithiol-3-thione

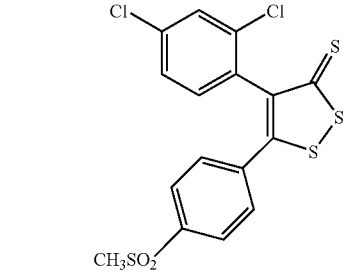

Formula 62

198 mg (yield 64%) of the titled compound as a liquid was prepared in the same manner as in Example 39 except using 0.3 g of 2-(2,4-dichlorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.94 (d, 2H, J=8.4 Hz), 7.50 (d, 2H, J=8.4 Hz), 7.43 (s, 1H), 7.30 (d, 1H, J=8.4 Hz), 7.07 (d, 1H, J=8.4 Hz), 3.07 (s, 3H)

EI Mass (M+): 433

Melting point: 176-177° C.

Example 59

4-(2-chloro-4-fluorophenyl)-5-(4-methanesulfonylphenyl)-[1,2]dithiol-3-thione

Formula 63

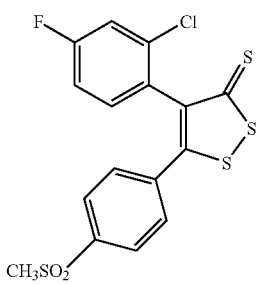

164 mg (yield 53%) of the titled compound as a liquid was prepared in the same manner as in Example 39 except using 0.3 g of 2-(2-chloro-4-fluorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.83 (d, 2H, J=8.4 Hz), 7.43 (d, 2H, J=8.4 Hz), 7.07 (dd, 1H, J=5.6 Hz, J=2.4 Hz), 7.03 (dd, 1H, J=8.4 Hz, J=6.0 Hz), 6.93 (td, 1H, J=6.0 Hz, J=2.4 Hz), 2.97 (s, 3H)

EI Mass (M+): 416

Melting point: 184-185° C.

Example 60

4-(3,4-dimethoxyphenyl)-5-(4-methanesulfonylphenyl)-[1,2]dithiol-3-thione

Formula 64

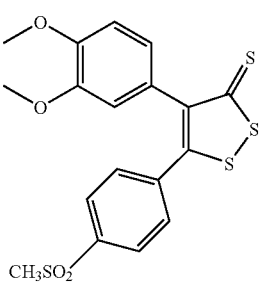

155 mg (yield 50%) of the titled compound as a liquid was prepared in the same manner as in Example 39 except using 0.3 g of 2-(3,4-dimethoxyphenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.81 (d, 2H, J=8.4 Hz), 7.40 (d, 2H, J=8.4 Hz), 6.73 (d, 1H, J=8.4 Hz), 6.61 (d, 1H, J=2.0 Hz), 6.53 (dd, 1H, J=7.2 Hz, J=2.0 Hz), 3.78 (s, 3H), 3.66 (s, 3H), 2.96 (s, 3H)

EI Mass (M+): 424

Melting point: 182-183° C.

Example 61

4-(2-bromophenyl)-5-(4-methanesulfonylphenyl)-[1,2]dithiol-3-thione

Formula 65

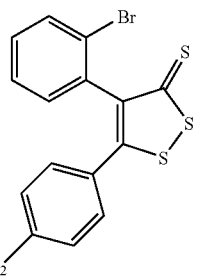

186 mg (yield 60%) of the titled compound as a liquid was prepared in the same manner as in Example 39 except using 0.3 g of 2-(2-bromophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.82 (d, 2H, J=8.4 Hz), 7.52-7.50 (m, 1H), 7.46 (d, 2H, J=8.4 Hz), 7.25-7.23 (m, 1H), 7.16-7.14 (m, 1H), 7.01-7.00 (m, 1H), 3.05 (s, 3H)

EI Mass (M+): 443

Melting point: 179-180° C.

Example 62

4-(2-fluorophenyl)-5-(4-methanesulfonylphenyl)-[1,2]dithiol-3-thione

Formula 66

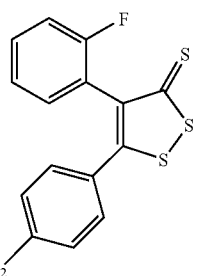

170 mg (yield 55%) of the titled compound as a liquid was prepared in the same manner as in Example 39 except using 0.3 g of 2-(2-fluorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.82 (d, 2H, J=8.4 Hz), 7.42 (d, 2H, J=8.4 Hz), 7.30-7.29 (m, 1H), 7.09-7.06 (m, 2H), 6.94 (t, 1H, J=9.3 Hz), 3.05 (s, 3H)

EI Mass (M+): 382

Melting point: 173-174° C.

Example 63

4-(2,4-difluorophenyl)-5-(4-methanesulfonylphenyl)-[1,2]dithiol-3-thione

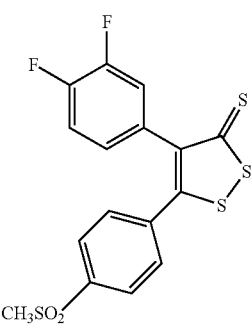

Formula 67

179 mg (yield 58%) of the titled compound as a liquid was prepared in the same manner as in Example 39 except using 0.3 g of 2-(2,4-difluoro)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.85 (d, 2H, J=8.4 Hz), 7.42 (d, 2H, J=8.4 Hz), 7.12 (dd, 1H, J=16.8 Hz, J=8.6 Hz), 6.87-6.84 (m, 1H), 6.69-6.66 (m, 1H), 3.0 (s, 3H)

EI Mass (M+): 400

Melting point: 148-149° C.

Example 64

4-(3,4-difluorophenyl)-5-(4-methanesulfonylphenyl)-[1,2]dithiol-3-thione

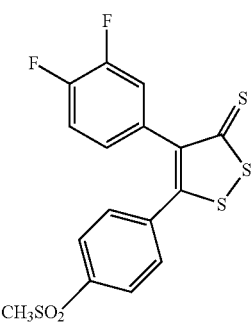

Formula 68

182 mg (yield 59%) of the titled compound as a liquid was prepared in the same manner as in Example 39 except using 0.3 g of 2-(3,4-difluorophenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.86 (d, 2H, J=8.4 Hz), 7.38 (d, 2H, J=8.4 Hz), 7.05-7.01 (m, 1H), 6.94-6.90 (m, 1H), 6.74-6.72 (m, 1H), 3.0 (s, 3H)

EI Mass (M+): 400

Melting point: 193-194° C.

Example 65

5-(4-methanesulfonylphenyl)-4-(naphthalene-2-yl)-[1,2]dithiol-3-thione

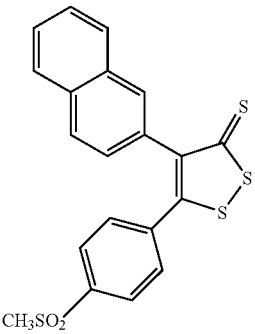

Formula 69

188 mg (yield 60%) of the titled compound as a liquid was prepared in the same manner as in Example 39 except using 0.3 g of 3-(4-methanesulfonylphenyl)-2-(naphthalene-2-yl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.93 (d, 2H, J=8.4 Hz), 7.70-7.65 (m, 6H), 7.37-7.35 (m, 3H), 3.04 (s, 3H)

EI Mass (M+): 414

Example 66

5-(4-methanesulfonylphenyl)-4-pentafluorophenyl-[1,2]dithiol-3-thione

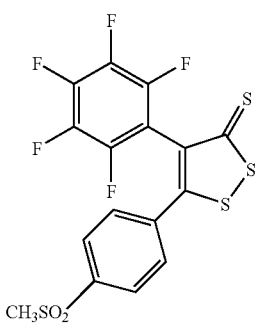

Formula 70

200 mg (yield 65%) of the titled compound as a liquid was prepared in the same manner as in Example 39 except using 0.3 g of 3-(4-methanesulfonylphenyl)-3-oxo-2-pentafluorophenyl-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 8.07 (d, 2H, J=8.4 Hz), 7.26 (d, 2H, J=8.4 Hz), 3H), 3.13 (s, 3H)

EI Mass (M+): 454

Melting point: 181-182° C.

Example 67

4-(4-isopropoxylphenyl)-5-(4-methanesulfonylphenyl)-[1,2]dithiol-3-thione

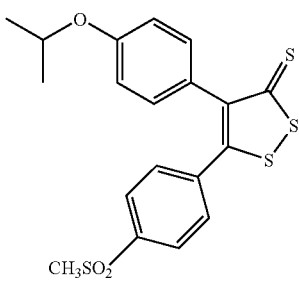

Formula 71

210 mg (yield 68%) of the titled compound as a liquid was prepared in the same manner as in Example 39 except using 0.3 g of 2-(4-isopropoxyphenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.90 (d, 2H, J=8.4 Hz), 7.47 (d, 2H, J=8.4 Hz), 7.06 (d, 2H, J=8.8 Hz), 6.84 (d, 2H, J=8.8 Hz), 4.52-4.50 (m, 1H), 3.06 (s, 3H), 1.32 (s, 3H), 1.31 (s, 3H)

EI Mass (M+): 422

Melting point: 179-180° C.

Example 68

5-(4-methanesulfonylphenyl)-4-(4-propoxyphenyl)-[1,2]dithiol-3-thione

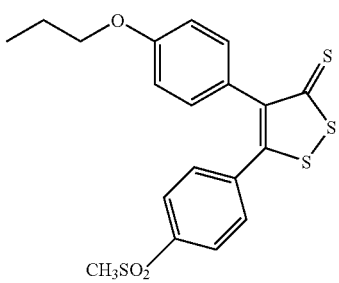

Formula 72

207 mg (yield 67%) of the titled compound as a liquid was prepared in the same manner as in Example 39 except using 0.3 g of 3-(4-methanesulfonylphenyl)-3-oxo-2-(4-propoxyphenyl)-propionic acid ethyl ester instead of 2-(4-ethoxyphenyl)-3-(4-methanesulfonylphenyl)-3-oxopropionic acid ethyl ester.

$^1$H-NMR (400 MHz, CDCl$_3$) δ 7.90 (d, 2H, J=8.4 Hz), 7.47 (d, 2H, J=8.4 Hz), 7.06 (d, 2H, J=8.8 Hz), 6.84 (d, 2H, J=8.8 Hz), 3.90 (s, 3H), 3.05 (s, 3H), 1.79-1.78 (m, 2H), 1.19 (t, 3H, J=8.0 Hz)

EI Mass (M+): 422

Melting point: 177-178° C.

Example 69

Acetic acid 4-[5-(4-methanesulfonylphenyl)-3-thioxo-3H-[1,2]dithiol-4-yl]phenyl ester

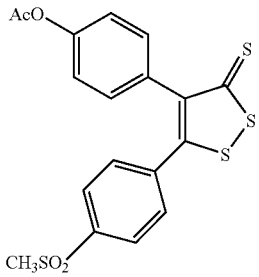

Formula 73

140 mg (yield 45%) of the titled compound as a liquid was prepared in the same manner as in Example 39 except using 0.3 g of 2-(4-acetoxyphenyl)-3-(4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.92 (d, 2H, J=9.4 Hz), 7.48 (d, 2H, J=9.4 Hz), 7.19 (d, 2H, J=7.6 Hz), 7.03 (d, 2H, J=7.6 Hz), 3.08 (s, 3H), 2.49 (s, 3H)

EI Mass (M+): 422

Melting point: 241-243° C.

Example 70

5-(2-chloro-4-methanesulfonylphenyl)-4-(4-ethoxyphenyl)-[1,2]dithiol-3-thione

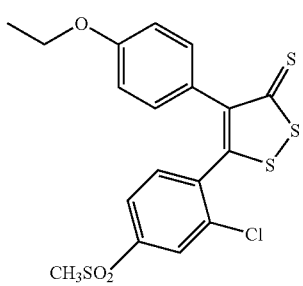

Formula 74

170 mg (yield 55%) of the titled compound as a liquid was prepared in the same manner as in Example 39 except using 0.3 g of 3-(2-chloro-4-methanesulfonylphenyl)-2-(4-ethoxyphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.80 (d, 1H, J=1.6 Hz), 7.69 (dd, 1H, J=6.4 Hz, J=2.0 Hz), 7.32 (d, 1H, J=8.0 Hz), 6.88 (d, 2H, J=8.4 Hz), 6.62 (d, 2H, J=8.4 Hz), 3.81 (q, 2H, J=7.2 Hz), 2.98 (s, 2H), 1.23 (t, 3H, J=4.0 Hz)

EI Mass (M+): 443

Melting point: 190-191° C.

Example 71

5-(2-chloro-4-methanesulfonylphenyl)-4-p-toryl-[1,2]dithiol-3-thione

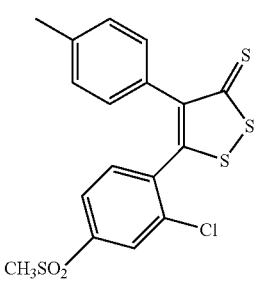

Formula 75

173 mg (yield 56%) of the titled compound as a liquid was prepared in the same manner as in Example 39 except using 0.3 g of 3-(2-chloro-4-methanesulfonylphenyl)-3-oxo-2-p-toryl-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.98 (d, 1H, J=1.6 Hz), 7.83 (dd, 1H, J=6.0 Hz, J=2.0 Hz), 7.51 (d, 1H, J=8.0 Hz), 7.11 (d, 2H, J=8.4 Hz), 7.02 (d, 2H, J=8.4 Hz), 3.09 (s, 3H), 2.32 (s, 3H)

EI Mass (M+): 413

Melting point: 188-189° C.

Example 72

4-(4-bromophenyl)-5-(2-chloro-4-methanesulfonylphenyl)-[1,2]dithiol-3-thione

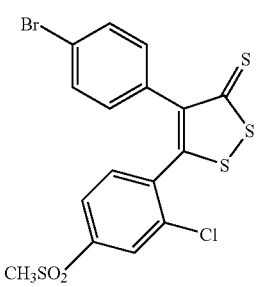

Formula 76

192 mg (yield 62%) of the titled compound as a liquid was prepared in the same manner as in Example 39 except using 0.3 g of 2-(4-bromophenyl)-3-(2-chloro-4-methanesulfonylphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.98 (d, 1H, J=1.6 Hz), 7.86 (dd, 1H, J=8.0 Hz, J=1.6 Hz), 7.51 (d, 1H, J=8.0 Hz), 7.11 (d, 2H, J=8.4 Hz), 7.02 (d, 2H, J=8.4 Hz), 3.09 (s, 3H)

EI Mass (M+): 477

Melting point: 194-195° C.

Example 73

5-(2-chloro-4-methanesulfonylphenyl)-4-(4-methoxyphenyl)-[1,2]dithiol-3-thione

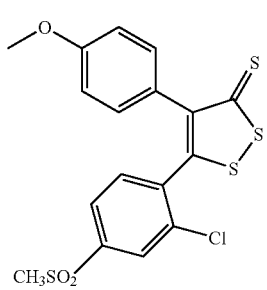

Formula 77

195 mg (yield 63%) of the titled compound as a liquid was prepared in the same manner as in Example 39 except using 0.3 g of 3-(2-chloro-4-methanesulfonylphenyl)-2-(4-methoxyphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.99 (d, 1H, J=1.6 Hz), 7.87 (dd, 1H, J=8.0 Hz, J=1.6 Hz), 7.52 (d, 1H, J=8.0 Hz), 7.12 (d, 2H, J=8.4 Hz), 7.03 (d, 2H, J=8.4 Hz), 4.25 (s, 3H), 3.09 (s, 3H)

EI Mass (M+): 428

Melting point: 192-193° C.

Example 74

5-(3,4-difluorophenyl)-4-p-toryl-[1,2]dithiol-3-thione

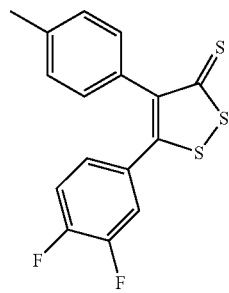

Formula 78

293 mg (yield 52%) of the titled compound as a liquid was prepared in the same manner as in Example 39 except using 0.5 g of 3-(3,4-difluorophenyl)-3-oxo-2-p-toryl-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.15 (d, 2H, J=7.6 Hz), 7.03-7.01 (m, 3H), 6.98 (d, 2H, J=7.6 Hz), 2.33 (s, 3H)

EI Mass (M+): 336

Melting point: 140-142° C.

Example 75

5-(3,4-difluorophenyl)-4-(4-methoxyphenyl)-[1,2]dithiol-3-thione

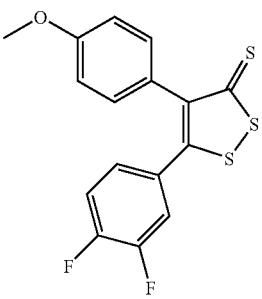

Formula 79

274 mg (yield 52%) of the titled compound as a liquid was prepared in the same manner as in Example 39 except using 0.5 g of 3-(3,4-difluorophenyl)-2-(4-methoxyphenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.16 (d, 2H, J=7.6 Hz), 7.04-7.02 (m, 3H), 6.99 (d, 2H, J=7.6 Hz), 3.82 (s, 3H)

EI Mass (M+): 352

Melting point: 143-145° C.

Example 76

Acetic acid 4-[5-(3,4-difluorophenyl)-3-thioxo-3H-[1,2]dithiol-4-yl]-phenyl ester

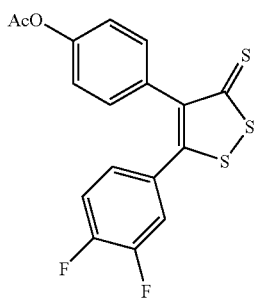

Formula 80

267 mg (yield 51%) of the titled compound as a liquid was prepared in the same manner as in Example 39 except using 0.5 g of 2-(4-acetoxyphenyl)-3-(3,4-difluorophenyl)-3-oxo-propionic acid ethyl ester instead of 2-(4-ethoxyphenyl)-3-(4-methanesulfonylphenyl)-3-oxo-propionic acid ethyl ester.

$^1$H-NMR (400 MHz, CDCl$_3$) δ 7.17 (d, 2H, J=7.6 Hz), 7.05-7.03 (m, 3H), 6.99 (d, 2H, J=7.6 Hz), 2.32 (s, 3H)

EI Mass (M+): 380

Melting point: 147-149° C.

Example 77

5-(3-fluoro-4-methanesulfonylphenyl)-4-p-toryl-[1,2]dithiol-3-thione

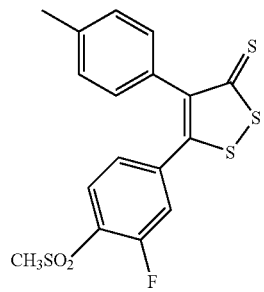

Formula 81

0.1 g of 5-(3,4-difluorophenyl)-4-p-toryl-[1,2]dithiol-3-thione which was prepared in the above example 74 was dissolved in dimethyl sulfoxide, and then 33 mg of sodium methanesulfinate was added thereto to let the mixture to react at 80° C. for 3 hours. When the reaction was completed, the reaction mixture was diluted with water and extracted with ethyl acetate. The obtained organic layer was dried on anhydrous magnesium sulfate and then purified by flash chromatography to give 66 mg of the titled compound as a red solid (yield 56%).

$^1$H-NMR (400 MHz, CDCl$_3$) δ 7.90-7.89 (m, 1H), 7.15-7.12 (m, 4H), 7.00-6.98 (m, 2H), 3.21 (s, 3H), 2.34 (s, 3H)

EI Mass (M+): 396

Melting point: 205-207° C.

Example 78

5-(3-fluoro-4-methanesulfonylphenyl)-4-(4-methoxyphenyl)-[1,2]dithiol-3-thione

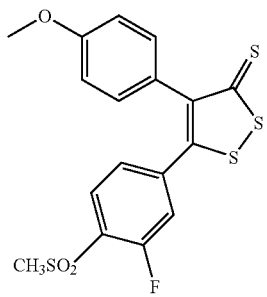

Formula 82

58 mg (yield 50%) of the titled compound as a solid was prepared in the same manner as in Example 78 except using 5-(3,4-difluorophenyl)-4-(4-methoxyphenyl)-[1,2]dithiol-3-thione which was prepared in the above example 75 instead of 5-(3,4-difluorophenyl)-4-p-toryl-[1,2]dithiol-3-thione.

$^1$H-NMR (400 MHz, CDCl$_3$) δ 7.85 (t, 1H, J=1.2 Hz), 7.17 (dd, 1H, J=10.0 Hz, J=2.0 Hz), 7.15 (dd, 1H, J=10.0 Hz, J=2.0 Hz), 6.96 (d, 2H, J=8.8 Hz), 6.84 (d, 2H, J=8.8 Hz), 3.74 (s, 3H), 3.20 (s, 3H)

EI Mass (M+): 352

Melting point: 150-152° C.

Example 79

Acetic acid 4-[5-(3-fluoro-4-methanesulfonylphenyl)-3-thioxo-3H-[1,2]dithiol-4-yl]-phenyl ester

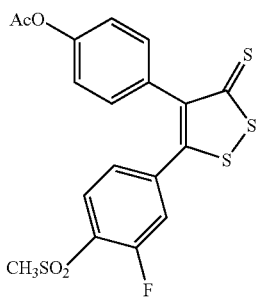

Formula 83

60 mg (yield 52%) of the titled compound as a solid was prepared in the same manner as in Example 78 except using acetic acid 4-[5-(3,4-difluorophenyl)-3-thioxo-3H-[1,2]dithiol-4-yl]-phenyl ester which was prepared in the above example 76 instead of 5-(3,4-difluorophenyl)-4-p-toryl-[1,2]dithiol-3-thione.

$^1$H-NMR (400 MHz, CDCl$_3$) δ 7.85 (t, 1H, J=1.2 Hz), 7.17-7.01 (m, 4H), 6.92 (d, 2H, J=8.0 Hz), 3.14 (s, 3H), 2.29 (s, 3H)

EI Mass (M+): 440
Melting point: 200-201° C.

Example 80

5-(4-methanesulfonylphenyl)-4-p-toryl-[1,2]dihydropyrazole-3-thione

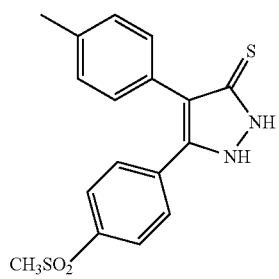

Formula 84

30 mg of potassium hydroxide was added to 0.1 g of 5-(4-methanesulfonylphenyl)-4-p-toryl-[1,2]dithiol-3-thione and then the mixture was dissolved in 5 ml of ethanol. Afterwards, 2 eq of hydrazine was added thereto to reflux at 80° C. for 12 hours. The color change from red to yellow was observed. Ethanol was distilled from the reaction mixture under reduced pressure, and the resultant was diluted with water and extracted with ethyl acetate. The obtained organic layer was dried on anhydrous magnesium sulfate to distill the solvent. The resultant was recrystallized with n-hexane to give 56 mg of the titled compound as a yellow solid (yield 62%).

$^1$H-NMR (400 MHz, CDCl$_3$) δ 7.86 (d, 2H, J=7.6 Hz), 7.58 (d, 2H, J=7.6 Hz), 7.22 (d, 2H, J=8.0 Hz), 7.16 (s, 2H, J=8.0 Hz), 3.04 (s, 3H), 2.38 (s, 3H)

EI Mass (M+): 344
Melting point: 198-200° C.

Example 81

4-(3,4-dichlorophenyl)-5-(4-methanesulfonylphenyl)-1,2-dihydropyrazole-3-thione

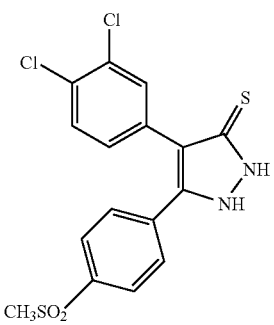

Formula 85

58 mg (yield 63%) of the titled compound as a liquid was prepared in the same manner as in Example 81 except using 0.1 g of 4-(3,4-dichlorophenyl)-5-(4-methanesulfonylphenyl)-[1,2]dithiol-3-thione instead of 5-(4-methanesulfonylphenyl)-4-p-toryl-[1,2]dithiol-3-thione.

$^1$H-NMR (400 MHz, CDCl$_3$) δ 7.83 (d, 2H, J=8.0 Hz), 7.58 (d, 2H, J=8.0 Hz), 7.50 (d, 1H, J=8.0 Hz), 7.16 (s, 1H), 7.07 (d, 1H, J=8.0 Hz), 3.20 (s, 3H)

FAB Mass (M+1): 399
Melting point: 192-193° C.

Example 82

4-(4-chlorophenyl)-5-(4-methanesulfonylphenyl)-1,2-dihydropyrazole-3-thione

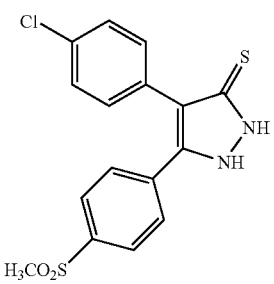

Formula 86

62 mg (yield 68%) of the titled compound as a liquid was prepared in the same manner as in Example 81 except using 0.1 g of 4-(4-chlorophenyl)-5-(4-methanesulfonylphenyl)-[1,2]dithiol-3-thione instead of 5-(4-methanesulfonylphenyl)-4-p-toryl-[1,2]dithiol-3-thione.

$^1$H-NMR (400 MHz, CDCl$_3$) δ 7.80 (d, 2H, J=8.0 Hz), 7.54 (d, 2H, J=8.0 Hz), 7.42 (d, 2H, J=8.4 Hz), 7.28 (d, 2H, J=8.4 Hz), 3.19 (s, 3H)

FAB Mass (M+1): 365
Melting point: 211-213° C.

Experiments

1. Evaluation of Selective COX-2 Inhibitory Activity

1) Method

In order to pharmacologically determine the selective COX-2 inhibitory activity, the percentages of the COX-1 and COX-2 inhibition of the compounds of the present invention illustrated in the Examples were measured by the following methods.

a. Assay for the COX-1 Inhibitory Activity Using U-937

U-937 human lymphoma cells (Korean Cell Line Bank, Seoul, Korea, Accession Number: 21593) were cultured and centrifuged. The collected cells were diluted with HBSS (×1, Hank's balanced salt solution) to a concentration of $1 \times 10^6$ cells/ml. 1 ml of the dilute cell solution was placed into each well of 12-well plates. 5 μl of 1 μM solution of a test compound in DMSO and 5 μl of DMSO as a control were added to the wells. The wells were incubated in $CO_2$ incubator at 37° C. for 15 minutes. Separately, 10 mM stock solution of arachidonic acid in ethanol was diluted ten times in ethanol to prepare 1 mM solution of arachidonic acid. Arachidonic acid acts as a substrate. 10 μl of the 1 mM solution of arachidonic acid was added to each well and incubated at $CO_2$ incubator at 37° C. for 30 minutes. The cell solution of each well was placed in a centrifuge test tube and centrifuged at 10,000 rpm at 4° C. for 5 minutes. The concentration of PGE2 in the collected cells and the supernatant was quantified by means of a monoclonal kit (Cayman Chemicals). The percentages of PGE2 inhibition in a group of the test compound-treated cells in relation to a group of the DMSO-treated cells were calculated. Based on the calculated values, the COX-1 inhibitory activities were evaluated.

b. Assay for the COX-2 Inhibitory Activity Using Raw 264.7 Cell Line $2 \times 10^6$ cells of RAW 264.7 cell line (Korean Cell Line Bank, Seoul, Korea, Accession Number: 40071) were inoculated into each well of 12-well plates. Each well was treated with 250 μM of aspirin and incubated at 37° C. for 2 hours. After the culture media were replaced with new culture media, the new culture media were treated with a test compound (30 nM) and incubated for 30 minutes. Then, each well was treated with interferon γ(100 units/ml) and lipopolysaccharide (LPS, 100 ng/ml) and incubated for 18 hours. The culture media were transferred to other test tubes. The concentration of PGE2 was quantified by means of the EIA kit (Cayman Chemicals).

2) Test results

The test results are presented in Table 1 below. The percentages of the COX inhibition were calculated according to the following equation:

% Inhibition=(concentration of PGE2 in test compound-untreated sample−concentration of PGE2 in test compound-treated sample)/(concentration of PGE2 in test compound-untreated sample)×100

TABLE 1

| Samples | Cyclooxygenase (COX) Inhibition (%) | |
|---|---|---|
| | COX-1 (1 μM) | COX-2 (30 nM) |
| Reference (Valdecoxib) | 28.8 | 19 |
| Example 39 | 15 | 36.6 |
| Example 40 | 18.3 | 35.7 |
| Example 41 | 20.1 | 24.5 |
| Example 42 | 24.5 | 20.1 |
| Example 43 | 19.3 | 38.4 |
| Example 44 | 25.5 | 20.1 |
| Example 45 | 19.6 | 22.1 |
| Example 46 | 24.6 | 21.0 |
| Example 47 | 22.5 | 21.4 |
| Example 48 | 23.6 | 24.2 |
| Example 49 | 28.0 | 19.5 |
| Example 50 | 27.2 | 19.6 |
| Example 51 | 27.6 | 19.8 |
| Example 52 | 26.6 | 19.1 |
| Example 53 | 26.7 | 21.6 |
| Example 54 | 22.4 | 26.3 |
| Example 55 | 27.6 | 20.2 |
| Example 56 | 20.6 | 25.6 |
| Example 57 | 20.7 | 21.1 |
| Example 58 | 24.2 | 20.1 |
| Example 59 | 23.2 | 19.7 |
| Example 60 | 26.5 | 19.3 |
| Example 61 | 23.3 | 20.1 |
| Example 62 | 26.6 | 21.0 |
| Example 63 | 20.3 | 21.3 |
| Example 64 | 21.6 | 19.8 |
| Example 65 | 22.6 | 20.1 |
| Example 66 | 28.2 | 19.2 |
| Example 67 | 27.5 | 23.3 |
| Example 68 | 25.5 | 22.7 |
| Example 69 | 24.8 | 21.3 |
| Example 70 | 17.5 | 36.0 |
| Example 71 | 20.3 | 21.0 |
| Example 72 | 28.1 | 19.3 |
| Example 73 | 25.6 | 20.1 |
| Example 74 | 26.5 | 19.2 |
| Example 75 | 26.6 | 19.6 |
| Example 76 | 21.6 | 20.3 |
| Example 77 | 15.2 | 31.5 |
| Example 78 | 18.5 | 32.5 |
| Example 79 | 19.5 | 30.2 |
| Example 80 | 25.6 | 23.2 |
| Example 81 | 24.9 | 24.6 |
| Example 82 | 24.3 | 22.2 |

3) Evaluation

The in vitro test results about the percentages of the COX-1 and COX-2 inhibition are listed in Table 1.

As shown in Table 1, inhibition (%) ratios of COX-2 to COX-1 in Examples 39 to 82 were significantly higher than that in the reference, Valdecoxib. This indicates that selective inhibition of COX-2 to COX-1 of the present compound is superior to that of the reference.

As is apparent from the above description, the thione derivative according to the present invention is an alternative drug for conventional nonsteroidal antiinflammatory agents and is expected to be useful for treating patients with peptic ulcer disease, gastritis, regional enteritis, ulcerative colitis, diverticullitis, gastrorrhagia, osteoarthritis, or rheumatoid arthritis.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A thione derivative represented by formula 1:

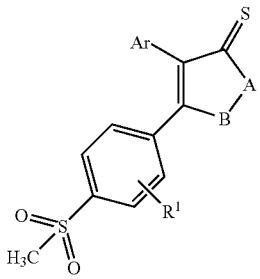

Formula 1 wherein:
A and B each independently represent O, S, $NR^2$; wherein $R^2$ represents hydrogen, $C_1$-$C_4$ alkyl, $C_1$-$C_4$ alkenyl, or aryl;
Ar represents aryl; heteroaryl; aryl or heteroaryl substituted with one to five radicals independently selected from the group consisting of $C_1$-$C_4$ alkyl, $C_1$-$C_4$ alkoxy, halogen, trifluoromethyl, nitro, acetoxy, amino, $C_1$-$C_3$ alkylamino, $C_1$-$C_3$ dialkylamino, hydroxy, $C_1$-$C_3$ hydroxyalkyl, and thioxy; and
$R^1$ represents hydrogen, $C_1$-$C_4$ alkyl, $C_1$-$C_4$ alkoxy, halogen, cyano, nitro, hydroxy, amino, $C_1$-$C_4$ alkylamino, or $C_1$-$C_4$ dialkylamino;
or a non-toxic salt thereof.

2. The thione derivative according to claim 1 wherein
A and B each independently represent S or NH;
Ar represents phenyl; phenyl substituted with one to five radicals independently selected from the group consisting of $C_1$-$C_4$ alkyl, $C_1$-$C_4$ alkoxy, halogen, trifluoromethyl, acetoxy, and nitro; pyridyl; or naphthyl;
$R^1$ represents hydrogen or halogen;
or a non-toxic salt thereof.

3. The thione derivative according to claim 1, which is selected from the group consisting of:
4-(4-ethoxyphenyl)-5-(4-methanesulfonylphenyl)-[1,2]dithiol-3-thione;
4-(4-bromophenyl)-5-(4-methanesulfonylphenyl)-[1,2]dithiol-3-thione;
5-(4-methanesulfonylphenyl)-4-toryl-[1,2]dithiol-3-thione;
5-(4-methanesulfonylphenyl)-4-phenyl-[1,2]dithiol-3-thione;
5-(4-methanesulfonylphenyl)-4-methoxyphenyl)-[1,2]dithiol-3-thione;
5-(4-methanesulfonylphenyl)-4-(2-trifluoromethylphenyl)-[1,2]dithiol-3-thione;
4-(4-chlorophenyl)-5-(4-methanesulfonylphenyl)-[1,2]dithiol-3-thione;
4-(3,4-dichlorophenyl)-5-(4-methanesulfonylphenyl)-[1,2]dithiol-3-thione;
5-(4-methanesulfonylphenyl)-4-pyridine-4-yl-[1,2]dithiol-3-thione;
5-(4-methanesulfonylphenyl)-4-pyridine-3-yl-[1,2]dithiol-3-thione;
5-(4-methanesulfonylphenyl)-4-pyridine-2-yl-[1,2]dithiol-3-thione;
4-(4-fluorophenyl)-5-(4-methanesulfonylphenyl)-[1,2]dithiol-3-thione;
4-(2,5-dimethoxyphenyl)-5-(4-methanesulfonylphenyl)-[1,2]dithiol-3-thione;
4-(3,5-dimethylphenyl)-5-(4-methanesulfonylphenyl)-[1,2]dithiol-3-thione;
5-(4-methanesulfonylphenyl)-4-(3-methoxyphenyl)-[1,2]dithiol-3-thione;
5-(4-methanesulfonylphenyl)-4-(2-nitrophenyl)-[1,2]dithiol-3-thione;
5-(4-methanesulfonylphenyl)-4-(3-trifluoromethylphenyl)-[1,2]dithiol-3-thione;
5-(4-methanesulfonylphenyl)-4-o-toryl-[1,2]dithiol-3-thione;
4-(2-chlorophenyl)-5-(4-methanesulfonylphenyl)-[1,2]dithiol-3-thione;
4-(2,4-dichlorophenyl)-5-(4-methanesulfonylphenyl)-[1,2]dithiol-3-thione;
4-(2-chloro-4-fluorophenyl)-5-(4-methanesulfonylphenyl)-[1,2]dithiol-3-thione;
4-(3,4-dimethoxyphenyl)-5-(4-methanesulfonylphenyl)-[1,2]dithiol-3-thione;
4-(2-bromophenyl)-5-(4-methanesulfonylphenyl)-[1,2]dithiol-3-thione;
4-(2-fluorophenyl)-5-(4-methanesulfonylphenyl)-[1,2]dithiol-3-thione;
4-(2,4-difluorophenyl)-5-(4-methanesulfonylphenyl)-[1,2]dithiol-3-thione;
4-(3,4-difluorophenyl)-5-(4-methanesulfonylphenyl)-[1,2]dithiol-3-thione;
5-(4-methanesulfonylphenyl)-4-naphthalene-2-yl-[1,2]dithiol-3-thione;
5-(4-methanesulfonylphenyl)-4-pentafluorophenyl-[1,2]dithiol-3-thione;
4-(4-isopropoxylphenyl)-5-(4-methanesulfonylphenyl)-[1,2]dithiol-3-thione;
5-(4-methanesulfonylphenyl)-4-(4-propoxyphenyl)-[1,2]dithiol-3-thione;
acetic acid 4-[5-(4-methanesulfonylphenyl)-3-thioxo-3H-[1,2]dithiol-4-yl]phenyl ester;
5-(2-chloro-4-methanesulfonylphenyl)-4-(4-ethoxyphenyl)-[1,2]dithiol-3-thione;
5-(2-chloro-4-methanesulfonylphenyl)-4-p-toryl-[1,2]dithiol-3-thione;
4-(4-bromophenyl)-5-(2-chloro-4-methanesulfonylphenyl)-[1,2]dithiol-3-thione;
5-(2-chloro-4-methanesulfonylphenyl)-4-(4-methoxyphenyl)-[1,2]dithiol-3-thione;
5-(3-fluoro-4-methanesulfonylphenyl)-4-p-toryl-[1,2]dithiol-3-thione;
5-(3-fluoro-4-methanesulfonylphenyl)-4-(4-methoxyphenyl)-[1,2]dithiol-3-thione;
acetic acid 4-[5-(3-fluoro-4-methanesulfonylphenyl)-3-thioxo-3H-[1,2]dithiol-4-yl]-phenyl ester;
5-(4-methanesulfonylphenyl)-4-p-toryl-1,2-dihydropyrazole-3-thione;
4-(3,4-dichlorophenyl)-5-(4-methanesulfonylphenyl)-1,2-dihydropyrazole-3-thione; and
4-(4-chlorophenyl)-5-(4-methanesulfonylphenyl)-1,2-dihydropyrazole-3-thione
or a non-toxic salt thereof.

4. A method for preparing a thione derivative of formula 1a or a non-toxic salt thereof, comprising reacting a propionic acid derivative of formula 2 with phosphorus pentasulfide, Lawesson's Reagent, beta-oxothioctic acid, or potassium beta-oxothioctate:

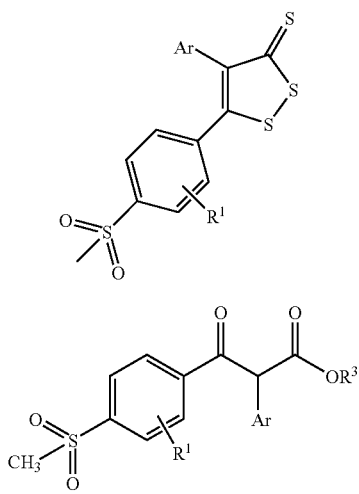

Formula 1a

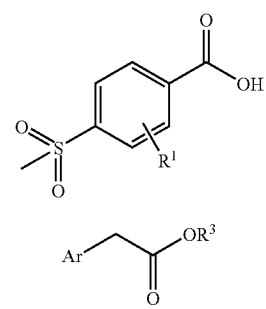

Formula 2 wherein:
R$^1$ and Ar are as defined in claim 1;
R$^3$ represents C$_1$-C$_3$ alkyl.

5. A method according to claim 4, wherein the propionic acid derivative of formula 2 is prepared by reacting a methanesulfonylbenzoic acid derivative of formula 3 with a aryl acetate derivative of formula 4 in the presence of a base;

Formula 3

Formula 4 wherein:
R$^1$ and Ar are as defined in claim 1 and R$^3$ represents C$_1$-C$_4$ alkyl.

6. A method for preparing a thione derivative of formula 1b or a non-toxic salt thereof, comprising reacting a thione derivative of formula 1a with NHR$^2$NH R$^2$ or NH R$^2$OH in the presence of a base;

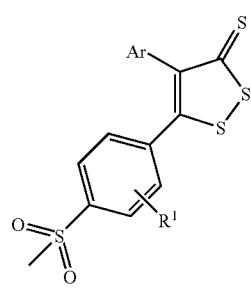

Formula 1a

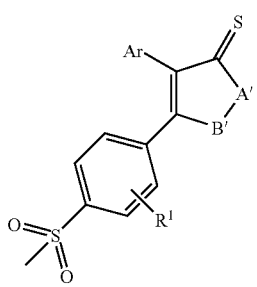

Formula 1b wherein:
A' and B' each independently represent S or NR$^2$, provided that A' and B' are not simultaneously S; and
Ar and R$^2$ are as defined in claim 1.

* * * * *